(12) United States Patent
Brandeis

(10) Patent No.: US 12,109,102 B2
(45) Date of Patent: Oct. 8, 2024

(54) AORTIC PROTECTION

(71) Applicant: Zeev Brandeis, Rosh HaAyin (IL)

(72) Inventor: Zeev Brandeis, Rosh HaAyin (IL)

( * ) Notice: Subject to any disclaimer, the term of this patent is extended or adjusted under 35 U.S.C. 154(b) by 0 days.

(21) Appl. No.: 16/650,918

(22) PCT Filed: Sep. 27, 2018

(86) PCT No.: PCT/IB2018/057501
§ 371 (c)(1),
(2) Date: Mar. 26, 2020

(87) PCT Pub. No.: WO2019/064223
PCT Pub. Date: Apr. 4, 2019

(65) Prior Publication Data
US 2020/0268500 A1    Aug. 27, 2020

Related U.S. Application Data

(60) Provisional application No. 62/564,314, filed on Sep. 28, 2017.

(51) Int. Cl.
*A61F 2/01*    (2006.01)
*A61F 2/00*    (2006.01)
*A61B 17/00*    (2006.01)

(52) U.S. Cl.
CPC .............. *A61F 2/01* (2013.01); *A61F 2/0105* (2020.05); *A61F 2/011* (2020.05); *A61B 2017/00778* (2013.01); *A61F 2002/0081* (2013.01); *A61F 2002/016* (2013.01); *A61F 2210/0014* (2013.01); *A61F 2210/0076* (2013.01); *A61F 2230/0013* (2013.01); *A61F 2230/0069* (2013.01); *A61F 2250/0004* (2013.01); *A61F 2250/0023* (2013.01)

(58) Field of Classification Search
CPC ................ A61F 2250/0004; A61F 2/01; A61F 2002/016; A61F 2002/0081; A61F 2/013
See application file for complete search history.

(56) References Cited

U.S. PATENT DOCUMENTS

| 6,258,120 | B1 * | 7/2001 | McKenzie | ....... A61B 17/12136 |
| | | | | 623/1.36 |
| 2001/0001114 | A1 | 5/2001 | Tsugita | |

(Continued)

FOREIGN PATENT DOCUMENTS

| EP | 2762083 | 8/2014 |
| EP | 3078350 | 10/2016 |

(Continued)

OTHER PUBLICATIONS

International Preliminary Report on Patentability Dated Apr. 9, 2020 From the International Bureau of WIPO Re. Application No. PCT/IB2018/057501. (9 Pages).

(Continued)

*Primary Examiner* — Tan-Uyen T Ho
*Assistant Examiner* — Bridget E. Rabaglia

(57) ABSTRACT

An aortic protection device including a mesh lumen shaped and sized to extend along the aorta, from a heart-side of a brachiocephalic artery exit from the aorta to distal of a left subclavian artery exit from the aorta, wherein the mesh lumen is arranged to change a porosity of mesh pores in response to external control. Related apparatus and methods are also described.

25 Claims, 31 Drawing Sheets

(56) References Cited

U.S. PATENT DOCUMENTS

| | | | |
|---|---|---|---|
| 2002/0077596 A1* | 6/2002 | McKenzie | A61F 2/07 606/195 |
| 2003/0171803 A1 | 9/2003 | Shimon | |
| 2004/0010308 A1 | 1/2004 | Zafrir-Pachter et al. | |
| 2004/0024416 A1* | 2/2004 | Yodfat | A61F 2/90 606/200 |
| 2004/0215167 A1* | 10/2004 | Belson | A61F 2/01 604/526 |
| 2004/0254523 A1 | 12/2004 | Fitzgerald | |
| 2006/0116715 A1* | 6/2006 | Khosravi | A61F 2/01 606/200 |
| 2007/0100430 A1* | 5/2007 | Rudakov | A61B 17/1214 623/1.13 |
| 2009/0270974 A1 | 10/2009 | Berez et al. | |
| 2012/0109183 A1 | 5/2012 | Belson | |
| 2013/0245669 A1* | 9/2013 | Basu | A61F 2/01 606/200 |
| 2013/0289716 A1 | 10/2013 | Don Michael | |
| 2014/0135815 A1 | 5/2014 | Hyde et al. | |
| 2016/0151141 A1 | 6/2016 | Zimmerman | |
| 2016/0175084 A1 | 6/2016 | Johnson | |
| 2016/0206452 A1* | 7/2016 | Berez | A61F 2/9662 |
| 2016/0324621 A1 | 11/2016 | Shezifi et al. | |
| 2017/0014232 A1 | 1/2017 | Ginn et al. | |
| 2017/0100144 A1* | 4/2017 | Zhadkevich | A61M 25/1011 |
| 2018/0207397 A1 | 7/2018 | Look et al. | |
| 2019/0000604 A1 | 1/2019 | Eli | |
| 2019/0380651 A1 | 12/2019 | Carreel et al. | |
| 2020/0069410 A1 | 3/2020 | Amans | |
| 2020/0297364 A1 | 9/2020 | Choe et al. | |
| 2022/0168087 A1 | 6/2022 | Pasquino et al. | |
| 2022/0192629 A1 | 6/2022 | Gifford, III et al. | |

FOREIGN PATENT DOCUMENTS

| | | | |
|---|---|---|---|
| JP | 2006-187627 | | 7/2006 |
| JP | 2012-523922 | | 10/2012 |
| JP | 2016-527002 | | 9/2016 |
| JP | 2017-131655 | | 8/2017 |
| WO | WO 2004/019817 | | 3/2004 |
| WO | WO-2015009655 A1 * | | 1/2015 ........... A61F 2/89 |
| WO | WO 2017/042808 | | 3/2017 |
| WO | WO 2018/148239 | | 8/2018 |
| WO | WO 2019/064223 | | 4/2019 |
| WO | WO 2024/038459 | | 2/2024 |
| WO | WO 2024/042527 | | 2/2024 |
| WO | WO 2024/042528 | | 2/2024 |
| WO | WO 2024/042529 | | 2/2024 |

OTHER PUBLICATIONS

International Search Report and the Written Opinion Dated Dec. 12, 2018 From the International Searching Authority Re. Application No. PCT/IB2018/057501. (16 Pages).
Alkhouli et al. "Embolic Protection Devices in Transcatheter Aortic Valve Replacement", JACC. Cardiovascular Interventions, 11(13):1274-1276, Jul. 1, 2018.
Boston Scientific "Reinventing PE Protection": 2P., Retrieved From Internet, 2020.
Boston Scientific "Sentry Clinical Trial—24 Months Data": 2P, Retrieved From Inernet, 2020.
Kleinbogard et al. "A Fresh Look at Coronary Microembolization", Nature Reviews Cardiology, 19(4): 265-280, Published Nov. 16, 1921.
Kroon et al. "Heterogeneity of Debris Captured by Cerebral Embolic Protection Filters During TAVI", Journal of Europe in Collaboration with the Working Group on Interventional Cardiology of the European Society of Cardiology, 16:1141-1147, Feb. 1, 2021.
Scalise "Aortic Lab Embrace Transcatheter Antiembolic Filter", CRT21 Virtual, 12.P, Retrieved from Internet, Feb. 2021.
Schmidt et al. "Debris Heterogeneity Across Different Valve Types Captured by a Cerebral Protection System During Transcatheter Aortic Valve Replacement", JACC. Cardiovascular Interventions, 11(13): 1262-1273, Jul. 1, 2018.
Notice of Reason(s) for Rejection Dated Apr. 18, 2023 From the Japan Patent Office Re. Application No. 2020-539150. (3 pages).
Communication Pursuant to Article 94(3) EPC Dated Jan. 10, 2023 From the European Patent Office Re. Application No. 18796107.3. (6 Pages).
Notice of Reasons for Rejection Dated Sep. 20, 2022 From the Japan Patent Office Re. Application No. 2020-539150. (6 Pages).
Translation Dated Oct. 6, 2022 of Notice of Reasons for Rejection Dated Sep. 20, 2022 From the Japan Patent Office Re. Application No. 2020-539150. (6 Pages).
International Search Report and the Written Opinion Dated Oct. 23, 2023 From the International Searching Authority Re. Application No. PCT/IL2023/050875 (14 Pages).
Invitation to Pay Additional Fees, Communication Relating to the Result of the Partial International Search and the Provisional Opinion Dated Nov. 23, 2023 From the International Searching Authority Re. Application No. PCT/IL2023/050900 (12 Pages).
International Search Report and the Written Opinion Dated Nov. 23, 2023 From the International Searching Authority Re. Application No. PCT/IL2023/050874 (8 Pages).
International Search Report and the Written Opinion Dated Jan. 26, 2024 From the International Searching Authority Re. Application No. PCT/IL.2023/050900 (21 Pages).
International Search Report and the Written Opinion Dated Nov. 23, 2023 From the International Searching Authority Re. Application No. PCT/IL2023/050901. (16 Pages).
International Search Report and the Written Opinion Dated Nov. 23, 2023 From the International Searching Authority Re. Application No. PCT/IL2023/050902. (16 Pages).
Arko et al. "Iliac Fixation Length and Resistance to In-Vivo Stentgraft Displacement", Journal of Vascular Surgery, 41(4): 664-671, Apr. 1, 2005.
Asenbaum et al. "Stent-Graft Surface Movement After Endovascular Aneurysm Repair: Baseline Parameters for Prediction, and Association with Migration and Stent-Graft-Related Endoleaks", European Rdiology, 29(12): 6385-6395, Published Jun. 27, 2019.
Bosman et al. The Proximal Fixation Strength of Modern EVAR Grafts in a Short Aneurysm Neck. An In Vitro Study, European Journal of Vascular and Endovascular Surgery, 39(2): 187-192, Feb. 2010.
Jiao et al. "Clinical Analysis of Acute Myocardial Infarction Caused by Coronary Embolism", Journal of Thoracic Discase, 9(9): 2898-2903, Sep. 2017.
Kariyanna et al. "Coronary Embolism and Myocardial Infarction: A Scoping Study", American Journal of Medical Case Reports, 8(2): 31-43, Published Online Dec. 17, 2019.
Kleinbongard et al. "A Fresh Look at Coronary Microembolization", Nature Reviews Cardiology, 19(4): 265-280, Published Online Nov. 16, 2021.
Leyva et al. "Myocardial Fibrosis Predicts Ventricular Arrhythmias and Sudden Death After Cardiac Electronic Device Implantation", Journal of the American College of Cardiology, 79(7): 665-678, Feb. 22, 2022.
Parato et al. "Aortic Regurgitation as A Risk Factor for Coronary Embolization From Complex Atheromatous Aortic Plaques: A Clinical Case", Jornal of Cardiovascular Echography, 29(2): 58-61, Apr.-Jun. 2019.
Roos et al. "Displacement Forces in Iliac Landing Zones and Stent Graft Interconnections in Endovascular Aortic Repair: An Experimental Study", European Journal of Vascular and Endovascular Surgery, 47(3): 262-267, Mar. 2014.
Translation Dated May 1, 2023 of Notice of Reason(s) for Rejection Dated Apr. 18, 2023 From the Japan Patent Office Re. Application No. 2020-539150. (3 pages).

* cited by examiner

AORTIC PROTECTION

RELATED APPLICATIONS

This application is a National Phase of PCT Patent Application No. PCT/IB2018/057501 having International filing date of Sep. 27, 2018, which claims the benefit of priority under 35 USC § 119(e) of U.S. Provisional Patent Application No. 62/564,314 filed on Sep. 28, 2017. The contents of the above applications are all incorporated by reference as if fully set forth herein in their entirety.

FIELD AND BACKGROUND OF THE INVENTION

The present invention, in some embodiments thereof, relates to a device inserted into an aorta and methods of using the device, and, more particularly, but not exclusively, to a cerebral aortic protection device and methods of using the device.

The disclosures of all references mentioned above and throughout the present specification, as well as the disclosures of all references mentioned in those references, are hereby incorporated herein by reference.

SUMMARY OF THE INVENTION

According to an aspect of some example embodiments a device is designed for insertion to an aorta, to block debris in blood from flowing to arteries.

According to an aspect of some example embodiments a device is designed for insertion to an aorta, capable of a controlled changing of porosity of a filter filtering blood flowing to arteries.

According to an aspect of some example embodiments a device is designed for insertion to an aorta, to protect aorta walls from tools passing along the aorta.

According to an aspect of some embodiments of the present invention there is provided an aortic protection device including a mesh lumen shaped and sized to extend along the aorta, from a heart-side of a brachiocephalic artery exit from the aorta to distal of a left subclavian artery exit from the aorta, wherein the mesh lumen is arranged to change a porosity of mesh pores in response to external control.

The term "mesh" in all its grammatical forms is used throughout the present specification and claims to mean a porous surface, whether constructed as a surface which includes pores, or as a weave which produces a porous mesh or net.

According to some example embodiments the mesh lumen is arranged to change a porosity from pores sized in a range between 200 microns and 100 microns to pores sized in a range between 100 and 50 microns or a range between 100 and 30 microns.

According to some example embodiments the mesh lumen includes a porous surface.

According to some example embodiments the mesh lumen includes a woven lumen.

According to some example embodiments an angle between a direction of a thread in an external side of the mesh lumen is configured to be less than 45 degrees from a direction of a longitudinal axis of the mesh lumen when the mesh lumen is deployed.

According to some embodiments of the invention, the device includes a first mesh lumen including shape-memory material and a second mesh lumen including flexible material co-axial with the first mesh lumen.

According to some embodiments of the invention, the first mesh lumen surrounds the second mesh lumen.

According to some embodiments of the invention, the second mesh lumen surrounds the first mesh lumen.

According to some embodiments of the invention, the first mesh lumen is attached to the second mesh lumen along most of a length of the first mesh lumen.

According to some embodiments of the invention, the first mesh lumen is not attached to the second mesh lumen along most of a length of the first mesh lumen.

According to some embodiments of the invention, the device includes a first mesh lumen including shape-memory material, a second mesh lumen including flexible material, and a third mesh lumen including flexible material, wherein the second mesh lumen and the third mesh lumen are co-axial with the first mesh lumen.

According to some embodiments of the invention, the first mesh lumen is attached to the third mesh lumen along most of a length of the first mesh lumen.

According to some embodiments of the invention, the first mesh lumen is not attached to the third mesh lumen along most of a length of the first mesh lumen.

According to some embodiments of the invention, a flexible material outside mesh lumen has a greater diameter than a shape memory inside mesh lumen, enabling the outside mesh lumen to extend into arteries branching off the aorta.

According to some embodiments of the invention, a flexible material inside mesh lumen is shaped to contract away from a shape memory outside mesh lumen, reducing pore size of the flexible material inside mesh lumen.

According to some embodiments of the invention, a flexible material inside mesh lumen is shaped to contract away from a shape memory outside mesh lumen, designed to increase flow rate with a smaller diameter of the flexible material inside mesh lumen.

According to some embodiments of the invention, the first mesh lumen is arranged to form an elongated shape with a horseshoe shaped cross section.

According to some embodiments of the invention, the shape memory material is a material selected from a group consisting of Nitinol, Nitinol alloy, stainless steel, DFT (Drawn Filled Tube) composite wire, cobalt chromium, polymer material such as polymer wire, polymer woven\braided material, a combination of more than one polymer, a medical grade metal coated with polymer, and polymer coated wire.

According to some embodiments of the invention, the flexible material is a material selected from a group consisting of polyurethane, carbonated polyurethane, a derivative of one of the above-mentioned materials, polymer, a mesh of polymer, polymer wire, woven polymer wire, polymer cable, and woven polymer cable.

According to an aspect of some embodiments of the present invention there is provided a method for protecting cerebral aorta from blood-borne debris during an aortic procedure, the method including inserting an aortic protection device including a first mesh lumen shaped and sized to extend along the aorta, from a heart-side of a brachiocephalic artery exit from the aorta to distal of a left subclavian artery exit from the aorta, inserting a surgical device for performing the aortic procedure, reducing porosity of the aortic protection device, and performing at least part of the aortic procedure.

According to an aspect of some example embodiments reducing porosity is performed by changing a porosity from pores sized in a range between 200 microns and 100 microns to pores sized in a range between 100 and 50 microns or a range between 100 and 30 microns.

According to some embodiments of the invention, the reducing porosity of the device includes twisting a proximal end of the first mesh lumen relative to a distal end of the first mesh lumen, thereby changing a shape of the mesh pores of the first mesh lumen and reducing porosity of the device.

According to some embodiments of the invention, the reducing porosity of the device includes deploying a second mesh lumen along at least a portion of the first mesh lumen, the second mesh lumen having smaller pores than the first mesh lumen.

According to some embodiments of the invention, the reducing porosity of the device includes deploying a second mesh lumen along at least a portion of the first mesh lumen, the second mesh lumen having pores a same size as the first mesh lumen.

According to some embodiments of the invention, the reducing porosity of the device includes rotating the second mesh lumen relative to the first mesh lumen.

According to some embodiments of the invention, the reducing porosity of the device includes twisting a proximal end of the second mesh lumen relative to a distal end of the second mesh lumen, thereby changing a shape of the mesh pores of the second mesh lumen and reducing porosity of the device.

According to some embodiments of the invention, inserting the device includes inserting the device including both the first mesh lumen and the second mesh lumen, wherein the second mesh lumen is packaged near a heart-side end of the first mesh lumen, and reducing porosity of the device includes un-packaging and deploying the second mesh lumen.

According to some embodiments of the invention, the reducing porosity of the device includes reducing a diameter of the device in response to external control.

According to some embodiments of the invention, the device includes a first mesh lumen including shape-memory material and a second mesh lumen including flexible material co-axial with the first mesh lumen, and the reducing the diameter of the device includes pulling out at least one wire included in the first mesh lumen.

According to some embodiments of the invention, the reducing porosity of the device includes extending a length of the device along the aorta.

According to some embodiments of the invention, the reducing porosity of the device includes reducing a length of the device along the aorta.

According to some embodiments of the invention, further including extracting the first mesh lumen in at least two stages, a first stage including pulling out at least one wire included in the first mesh lumen and a subsequent stage including pulling out a remainder of the wires included in the first mesh lumen.

According to some embodiments of the invention, further including extracting the first mesh lumen before extracting the second mesh lumen.

According to some embodiments of the invention, further including extracting the second mesh lumen before extracting the first mesh lumen.

According to some embodiments of the invention, the aortic procedure includes a procedure selected from a group consisting of a trans-catheter aortic valve implantation (TAVI), a trans-catheter aortic valve replacement (TAVR), and a percutaneous aortic valve replacement (PAVR).

According to an aspect of some embodiments of the present invention there is provided a method for protecting cerebral aorta from blood-borne debris during an aortic valve procedure, the method including inserting a device including a first mesh lumen including shape-memory material and a second mesh lumen including flexible material co-axial with the first mesh lumen, both of the mesh lumens shaped and sized to extend along the aorta, from a heart-side of a brachiocephalic artery exit from the aorta to distal of a left subclavian artery exit from the aorta, inserting a surgical device for performing the aortic valve procedure, and performing at least part of the aortic procedure, wherein the second mesh lumen is not attached to the first mesh lumen at least along entrances to a brachiocephalic artery, a left common carotid artery and a left subclavian artery.

According to an aspect of some embodiments of the present invention there is provided a method of manufacturing an aortic protection device including producing a mesh lumen shaped and sized to extend along the aorta, from a heart-side of a brachiocephalic artery exit from the aorta to distal of a left subclavian artery exit from the aorta, wherein the mesh lumen is arranged to change a porosity of mesh pores in response to external control.

According to some embodiments of the invention, the mesh lumen is produced of a material selected from a group consisting of a polyurethane material, a carbonated polyurethane material, and a derivative of one of the above-mentioned materials.

According to some embodiments of the invention, the mesh lumen includes a porous surface.

According to some embodiments of the invention, the mesh lumen includes a woven lumen.

According to some embodiments of the invention, further including producing the woven lumen by weaving the woven lumen.

According to some embodiments of the invention, an angle between a direction of a thread in an external side of the mesh lumen is configured to be less than 45 degrees from a direction of a longitudinal axis of the mesh lumen when the mesh lumen is deployed.

According to some embodiments of the invention, the producing the device includes producing a first mesh lumen including shape-memory material and a second mesh lumen including flexible material co-axial with the first mesh lumen.

According to some embodiments of the invention, the device is produced so that the first mesh lumen surrounds the second mesh lumen.

According to some embodiments of the invention, the device is produced so that the second mesh lumen surrounds the first mesh lumen.

According to some embodiments of the invention, the device the device is produced to include a first mesh lumen including shape-memory material, a second mesh lumen including flexible material, and a third mesh lumen including flexible material, wherein the second mesh lumen and the third mesh lumen are co-axial with the first mesh lumen.

According to some embodiments of the invention, the device is produced so that the first mesh lumen is attached to the third mesh lumen along most of a length of the first mesh lumen.

According to some embodiments of the invention, the device is produced so that the first mesh lumen is not attached to the third mesh lumen along most of a length of the first mesh lumen.

According to some embodiments of the invention, the shape memory material is a material selected from a group consisting of Nitinol, Nitinol alloy, stainless steel, DFT (Drawn Filled Tube) composite wire, cobalt chromium, polymer material such as polymer wire, polymer woven\braided material, a combination of more than one polymer, a medical grade metal coated with polymer, and polymer coated wire.

According to some embodiments of the invention, the flexible material is a material selected from a group consisting of polyurethane, carbonated polyurethane, a derivative of one of the above-mentioned materials, polymer, a mesh of polymer, polymer wire, woven polymer wire, polymer cable, and woven polymer cable.

According to some embodiments of the invention, the flexible material is produced by a production process selected from a group consisting of polymer injection, dipping a cylindrical shape in polymer, overcoating a cylindrical shape or sleeve in polymer, electro-spinning a polymer thread, and weaving polymer threads.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
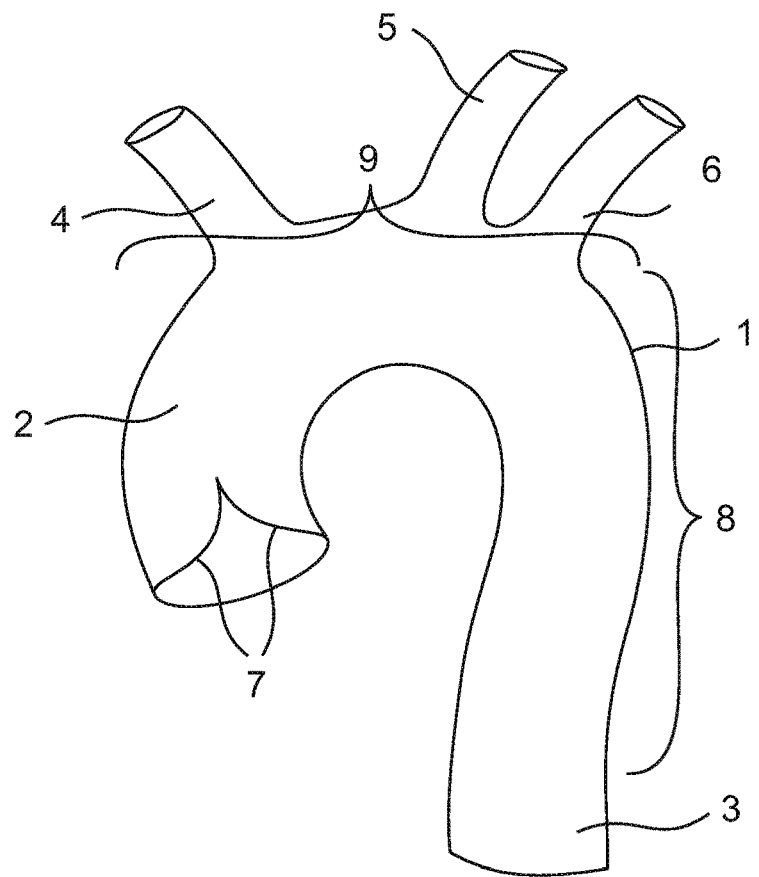
FIG. 1 is a simplified line drawing illustration of a section of an aorta.

The present invention, in some embodiments thereof, relates to a device inserted into an aorta and methods of using the device, and, more particularly, but not exclusively, to a cerebral aortic protection device and methods of using the device.

An aspect of some embodiments of the invention includes a device which includes a mesh lumen which is arranged to change porosity through lumen walls.

In some embodiments, the device includes a mesh lumen which changes its porosity in response to being twisted.

In some embodiments, the device includes two layers of mesh, and porosity through the two layers changes in response to a first mesh layer shifting and/or twisting relative to a second mesh layer.

In some embodiments, the device includes a first layer of mesh with a first porosity through the first layer, and a second layer of mesh deployable to lie parallel and/or concentric to the first layer, the two layers together optionally having a different porosity than the first layer alone.

In some embodiments the device is arranged to be inserted and deployed in an aorta with the second mesh layer furled and/or folded such that the second mesh extends along a small portion, for example less than half, of the first mesh lumen is covered by the second mesh. In some embodiments the second mesh lumen is optionally unfurled and/or unfolded within an aorta and deployed to lie parallel to the first mesh lumen, optionally along a significant portion of a length of the first mesh lumen, optionally along an entire length of the first mesh lumen.

In some embodiments, the device includes a first layer of mesh with a first porosity, and a second mesh layer lumen of shape memory wires deployable to lie parallel and/or concentric to the first layer. In some embodiments at least one of the wires of the second layer are arranged to be optionally pulled out of at least a portion of the second mesh layer, optionally enabling a partial collapse of the second mesh layer, optionally enabling the first mesh layer to contract and change porosity of the first mesh layer.

In some embodiments, the device includes a mechanism for changing a length of at least a first layer of mesh with a first porosity, optionally stretching the first layer, optionally changing the porosity of the first layer. In some embodiments, the device includes a mechanism for changing a length of at least a first layer of mesh with a first porosity, optionally contracting a length of the first layer, optionally changing the porosity of the first layer.

In some embodiments, the device includes three layers of mesh. In some embodiments the layers include a first, outer layer, a second middle layer, and a third, inner layer.

In some embodiments, the device includes two layers. In some embodiments the layers include a first, outer layer, and a second inner layer including shape memory wires.

In some embodiments, the device includes two layers. In some embodiments the layers include a first, outer layer including shape memory wires, and a second inner layer.

In some embodiments, the shape memory layer optionally gives a deployed device a shape of a lumen, optionally corresponding to an inside of an aorta.

In some embodiments, an outer layer of the device is flexible. In some embodiments, when the device is deployed in an aorta, blood pressure optionally pushes an outer mesh layer into artery openings in a wall of the aorta.

In some embodiments, an inner layer of the device is flexible. In some embodiments, when the device is deployed in an aorta, blood flow through the inner layer optionally lowers pressure within the inner layer, optionally causing the inner layer to contract. In some embodiments the inner layer optionally changes porosity due to the contracting. In some embodiments the inner layer contracting and forming a narrower lumen increases blood flow rate through the device, potentially clearing blood debris from the inside of the lumen.

An aspect of some embodiments of the invention includes inserting a device which includes a mesh lumen which is arranged to change porosity into an aorta, deploying the device, and changing the porosity of the mesh lumen when the device is within the aorta.

In some embodiments changing the porosity includes twisting a first portion of the mesh lumen relative to a second portion of the mesh lumen. In some embodiments the twisting is performed by twisting a first wire connected to the first portion of the mesh a different amount and/or a different direction than a second wire connected to the second portion of the mesh.

In some embodiments, the device includes two layers of mesh, and changing the porosity through the two layers includes shifting and/or twisting a first mesh layer relative to a second mesh layer.

In some embodiments, the device includes two layers of mesh. A first layer of mesh is initially deployed, and changing the porosity includes deploying the second layer of mesh to lie parallel and/or concentric to the first layer of mesh.

In some embodiments, the device includes a first layer of mesh with a first porosity, and a second mesh layer lumen of shape memory wires, in some embodiments, changing the porosity includes optionally pulling out at least a portion of the second mesh layer, optionally enabling a partial collapse of the second mesh layer, optionally enabling the first mesh layer to contract and change porosity of the first mesh layer.

In some embodiments, the device includes two layers of mesh. In some embodiments, changing porosity includes changing a length of at least a first layer of mesh, optionally stretching the first layer, optionally changing the porosity of the first layer.

An aspect of some embodiments of the invention includes extracting a device which includes a mesh lumen from an aorta.

In some embodiments the device is pulled into a catheter, and the catheter is extracted from the aorta and from the body.

In some embodiments the catheter is inserted via a trans-femoral route. In some embodiments the catheter is inserted via a radial route. In some embodiments the catheter is inserted through an open blood vessel during open heart surgery. In some embodiments catheters used for insertion have a diameter of, by way of a non-limiting example, 6, 8, and 10 French. In some embodiments the device includes lead wires from one end of the device—when the lead wires are pulled into a catheter, the device is pulled after the lead wires into the catheter, optionally furling into a small diameter suitable for entering the catheter.

The term "catheter" is used throughout the present specification and claims interchangeably with the term "sheath".

In some embodiments the device is pulled into a catheter in one stage and/or one pull, and the catheter is extracted from the aorta and from the body In some embodiments the device is pulled into a catheter in more than one stage and/or more than one pull. In some stages the catheter includes a wire mesh, and some of the wires are pulled into a catheter at a first stage, and some of the wires are pulled into the catheter at a subsequent stage.

In some embodiments the device includes a mesh on a downstream end of a mesh lumen. In some embodiments the mesh at the downstream end potentially traps debris flowing in the blood stream. In some embodiments when the device is pulled into a catheter for extraction, the debris is enveloped in the device, and the debris is pulled into the catheter with the device.

An aspect of some embodiments of the invention includes inserting a device which includes two layers of mesh lumen to an aorta, and allowing an outer one of the two layers to be swept into artery openings in the aorta, to provide a mesh across the artery openings, potentially preventing debris from entering the arteries.

An aspect of some embodiments of the invention includes inserting a device which includes a mesh lumen which is arranged to change porosity into an aorta, deploying the device in the aorta, and inserting tools for surgery on a heart through the device.

In some embodiments the mesh lumen protects walls of the aorta from the tools. In some embodiments a material forming an inside of the device is made slippery, to aid insertion of the tools for surgery on the heart through the aorta.

For purposes of better understanding some embodiments of the present invention, reference is first made to FIG. 1, which is a simplified line drawing illustration of a section of an aorta.

FIG. 1 shows a section of an aorta 1. A first end 2 of the section of the aorta 1 is an end near the heart (not shown), and a second end 3 of the section of the aorta 1 is an end more distant from the heart. FIG. 1 shows an aortic arch, and second end 3 corresponds to a descending thoracic aorta.

The section of the aorta 1 is shown with exits to a few major arteries: a first, proximal-to-the-heart exit is to a brachiocephalic artery 4; a second exit is to a left common carotid artery 5; and a third exit is to a left subclavian artery 6.

It is noted that the brachiocephalic artery 4 supplies blood to a right common carotid artery. The right and the left common carotid arteries supply blood to a brain. When an operation is performed on a heart, it happens that debris from the operation, by way of a non-limiting example calcium from a calcified heart valve, may detach from the heart and flow with the blood stream. If such debris flows to the brain, the debris may block an artery in the brain, as the arteries' diameter becomes smaller.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Before explaining at least one embodiment of the invention in detail, it is to be understood that the invention is not necessarily limited in its application to the details set forth in the following description. The invention is capable of other embodiments or of being practiced or carried out in various ways.

Figure 2A:
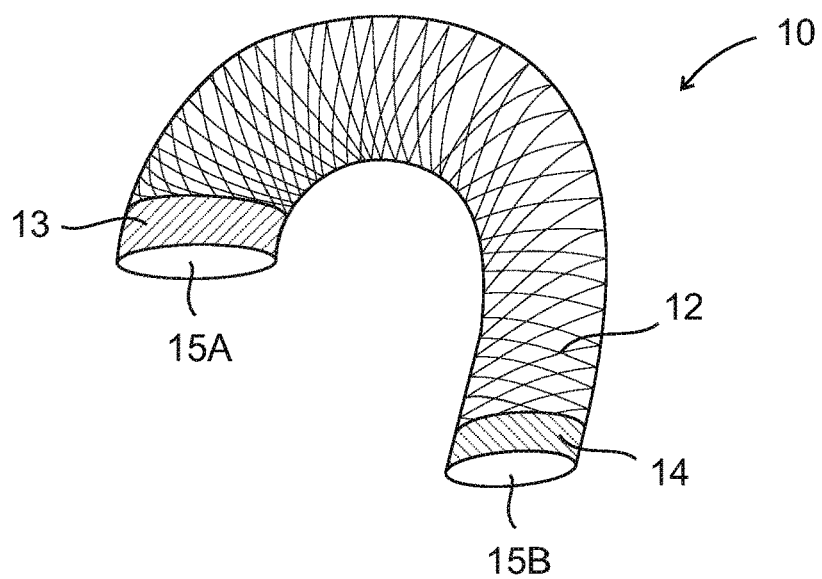
FIG. 2A is a simplified line drawing illustration of an aortic protection device, according to an example embodiment of the invention.

Reference is now made to FIG. 2A, which is a simplified line drawing illustration of an aortic protection device, according to an example embodiment of the invention.

In some embodiments of the invention an aortic protection device 10 is inserted into the aorta. The device 10 optionally extends from near the first end 2 of the section of the aorta 1 shown in FIG. 1, to the second end 3 of the section of the aorta 1 shown in FIG. 1.

In some embodiments the device may optionally be sized and shaped to extend further down the descending thoracic aorta, and even along the abdominal aorta. Description of embodiments of the device and methods of using the device apply also to a longer device extending further, as can be understood by a person skilled in the art.

The device 10 includes a mesh 12, optionally in a shape of a lumen. In some embodiments the device 10 optionally includes a heart-proximal ring 13, at a heart-proximal end 15A of the mesh 12.

In some embodiments the heart-proximal ring 13 optionally anchors the device 10 to the aorta, optionally preventing movement of the device along the aorta while other tools or catheter(s) (not shown) pass through the device 10. In some embodiments the heart-proximal ring 13 optionally pushes against walls of the aorta in order to anchor the device 10 to the aorta.

In some embodiments one or more mesh layers are attached to the heart-proximal ring 13.

In some embodiments the device 10 optionally includes a heart-distal ring 14, at a heart-distal end 15B of the mesh 12.

In some embodiments, the device 10 is sized and shaped to fit an inside of an aorta of a patient.

In some embodiments, the size of the device 10 is selected from a range of sizes, lengths and diameters of the device, to fit patients from small to large.

In some embodiments, a length of the aortic protection device 10 is in a range of 100 to 200 to 250 millimeters.

In some embodiments the device may optionally be sized and shaped to extend further down the descending thoracic aorta, and even along the abdominal aorta, and reach a length up to 450 millimeters.

In some embodiments the device may optionally be sized and shaped to have a diameter of 20 to 28 to 45 to 70 millimeters, optionally to correspond to a diameter of a patient's aorta.

FIG. 2A, as well as the others Figures in the present specification, are not necessarily drawn to an exact scale. By way of example, holes in the mesh 12 are not necessarily drawn to scale.

In some embodiments the device 10 includes a layer of wires including shape memory material, optionally giving the device 10 its shape, when deployed, and one or more layers of mesh with small pores, sized in a range from X to Y microns.

In some embodiments mesh hole sizes depend on how much the mesh is stretched, for example by a shape of the shape-memory material.

Some non-limiting examples of the layer of shape memory material include a mesh made from shape memory material, a mesh woven and/or braided from shape memory material, and shape memory wires placed parallel to additional layers in the device.

Some non-limiting example of shape memory material include: Nitinol; Nitinol alloy; stainless steel; DFT (Drawn Filled Tube) composite wire; cobalt chromium; polymer material such as polymer wire; polymer woven\braided material; a combination of more than one polymer; medical grade metal coated with polymer; optionally in a form of wires\tubes and/or in a braided or laser cut form; thin polymer strings of high strength and flexibility, similar to memory-shaped polymer materials.

In some embodiments a polymer mesh potentially protects the aortic wall and/or calcification of the aortic wall from damage which may be inflicted by stiffer material such as a metal or plastic wire in the device.

In some embodiments the polymer mesh protects the aortic wall by being a softer or more elastic material than the stiffer material.

In some embodiments the polymer mesh is made of a polyurethane material or a carbonated polyurethane material or a derivative of the above-mentioned materials. In some embodiments the derivative material has same traits and/or characteristics as the polyurethane material or the carbonated polyurethane material.

In some embodiments the polymer mesh is made by injection of the polymer.

In some embodiments the polymer mesh is made by dipping a cylindrical shape or sleeve in the polymer material.

In some embodiments the polymer mesh is made by overcoating a cylindrical shape or sleeve in the polymer material.

In some embodiments the polymer mesh is made by weaving a polymer thread produced by electro-spinning a polymer material. In some embodiments the thread is electro-spun to a diameter in a range between 10 microns and 1 micron. In some embodiments the thread is electro-spun to a diameter lower than 1 micron, down to 0.5 micron.

In some embodiments the polymer mesh is made by weaving polymer threads. In some embodiments the weaving is a directional weaving. In some embodiments the weaving is a non-directional weaving, or weaving in random directions.

In some embodiments the polymer mesh is made of a smooth material, potentially suitable for sliding along a wall of the aorta.

In some embodiments the polymer mesh is made of a slippery material, potentially suitable for sliding along a wall of the aorta.

In some embodiments the polymer mesh is made of a non-stick or non-adhesive material, potentially suitable for sliding along a wall of the aorta.

In some embodiments the polymer mesh protects the aortic wall by using a weave of the mesh which prevents the stiffer material from touching the aortic wall.

In some embodiments the polymer mesh protects the aortic wall by using a weave of the mesh which enables the mesh to slide along the aortic wall.

In some embodiments an angle between a thread direction of the external side of the mesh and a direction of a longitudinal axis of the mesh lumen when the mesh lumen is deployed is configured to be less than an angle of 5 degrees, 10 degrees, 15 degrees, 20 degrees, 30 degrees, 35 degrees, 40 degrees, or 45 degrees or other angles in that range.

In some embodiments the device 10 is optionally attached to the aortic wall.

In some embodiments the device 10 is optionally inserted into an aorta and then expanded to press against the aortic wall.

In some embodiments contact between the device 10 and the aortic wall is based on outward radial pressure of a polymer mesh in the heart-proximal ring 13 pressing onto the aortic wall. Such pressure potentially fixes the heart-proximal ring 13 so as not to slide along the aortic wall. The pressure potentially fixes the heart-proximal ring 13 and does not damage the aortic wall and/or potentially does not cause the aortic wall to release particles downstream.

In some embodiments, the heart-proximal ring 13 is optionally shrunk to a lower diameter before pulling the device 10 out of the aorta. In some embodiments the shrinking is optionally performed by removing some wires, such as the Nitinol wires described below, from the heart-proximal ring 13. In some embodiments the shrinking is optionally performed by reducing the outward radial force on the wall of the aorta. In some embodiments the shape and/or outward pressure of the heart-proximal ring 13 is optionally controlled by one or more wires such as a trigger wire and/or a first wire 217 and/or connecting wires 218A 218B descried below with reference to FIG. 2B.

In some embodiments, the heart-proximal ring 13 is optionally the first portion of the device 10 to be pulled out of the aorta.

In some embodiments, the heart-proximal ring 13 is optionally the first portion of the device 10 to be pulled into a catheter for extracting the device 10 from the aorta.

In some embodiments the heart-proximal ring 13 and/or the device 10 optionally include Nitinol wires. In some embodiments the Nitinol wires are pulled out of the aorta and/or into a catheter for extraction before a polymer mesh portion of the device 10 is pulled out of the aorta and/or into a catheter for extraction.

In some embodiments the device 100 is optionally pulled out of the aorta and/or a patient's body without shrinking into a catheter.

In some embodiments the device 100 is optionally compressed into a catheter such as an introducing catheter for removing from the patient's body.

In some embodiments, wires such as Nitinol wires are optionally taken out of the device 100, and then the rest of the device 100 is optionally pulled out of the aorta and/or the patient's body, and/or compressed into a catheter such as an introducing catheter for removing from the patient's body.

Figure 2B:
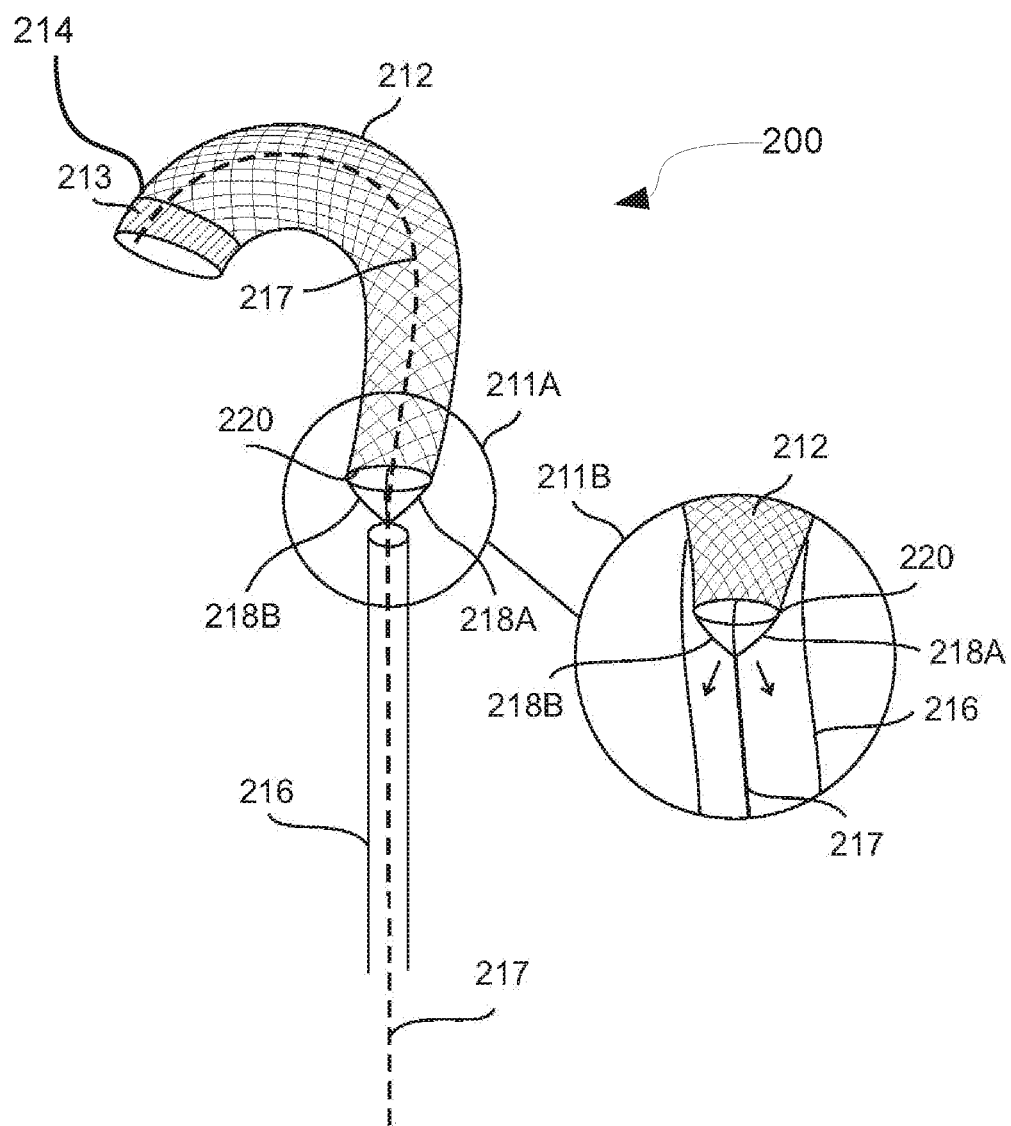
FIG. 2B is a simplified line drawing illustration of an example embodiment of the invention.

Reference is now made to FIG. 2B, which is a simplified line drawing illustration of an example embodiment of the invention.

FIG. 2B shows a device 200 including a mesh 212, an optional heart-proximal ring 213 at a heart-proximal end of the mesh 212, and the device connected to a first wire 217.

A heart-distal end 220 of the mesh 212 is optionally connected to the first wire 217 by connecting wires 218A 218B.

The mesh 212 is shown deployed, expanded to an inner diameter of an aorta (not shown), with a catheter 216 near the heart-distal end 220 of the mesh 212. The connecting wires 218A 218B spread out from the first wire 217 to the heart-distal end 220 of the mesh 212.

In some embodiments the optional heart-proximal ring 213 optionally anchors the device 200 to the aorta, optionally preventing movement of the device along the aorta while other tools or catheter(s) (not shown) pass through the device 200. In some embodiments the heart-proximal ring 213 optionally pushes against walls of the aorta in order to anchor the device 200 to the aorta, In some embodiments one or more mesh layers are attached to the heart-proximal ring 213.

In some embodiments the connecting wires 218A 218B are arranged to potentially assist in withdrawing the mesh 212 back into the catheter 216. The potential assistance in withdrawing is provided by the connecting wires attached to the first wire 217 so that when the first wire 217 is pulled back relative to the catheter 216 the connecting wires 218A 218B pull edges of the mesh 212 to which they are connected into the catheter 216.

FIG. 2B shows a first circled portion 211A which shows the mesh 212, connecting wires 218A 218B and the first wire 217, in a drawing where the mesh 212 is deployed outside the catheter 216.

FIG. 2B shows a second circled portion 211B which shows the mesh 212, connecting wires 218A 218B and the first wire 217, in a drawing where the mesh 212 is partly inside the catheter 216.

In some embodiments anchoring of the device 200 to the aortic wall is optionally based on outward radial pressure of a polymer mesh in the optional heart-proximal ring 213 pressing onto the aortic wall. Such pressure potentially fixes the heart-proximal ring 213 so as not to slide along the aortic wall. The pressure potentially fixes the heart-proximal ring 213 and does not damage the aortic wall and/or potentially does not cause the aortic wall to release particles downstream.

In some embodiments, the heart-proximal ring 213 is optionally shrunk to a lower diameter before pulling the device 200 out of the aorta. In some embodiments the shrinking is optionally performed by removing one or more wires, for example a wire 214, for example made of material such as the Nitinol wires described below, from the heart-proximal ring 213. In some embodiments the shrinking is optionally performed by reducing the outward radial force on the wall of the aorta. In some embodiments the shape and/or outward pressure of the heart-proximal ring 213 is optionally controlled by one or more wires such as a trigger wire and/or the first wire 217 and/or the connecting wires 218A 218B. In some embodiments the heart-proximal ring 213 collapses to a conical shape or a cylindrical shape.

In some embodiments, the heart-proximal ring 213 is optionally the first portion of the device 200 to be pulled out of the aorta.

In some embodiments the heart-proximal ring 213 is collapsed, and the heart-proximal ring 213 is optionally pulled by the first wire 217, turning the device 200 inside-out, pulling the heart-proximal ring 213 toward the catheter 216.

In some embodiments, the heart-proximal ring 213 is optionally the first portion of the device 200 to be pulled into the catheter 216 for extracting the device 200 from the aorta.

In some embodiments the heart-proximal ring 213 and/or the device 200 optionally include Nitinol wires.

In some embodiments the Nitinol wires are pulled out of the aorta and/or into a catheter for extraction before a polymer mesh portion of the device 200 is pulled out of the aorta and/or into a catheter for extraction.

In some embodiments the shape and/or outward pressure of the heart-proximal ring 213 is optionally controlled by one or more wires such as a trigger wire and/or the first wire 217 and/or the connecting wires 218A 218B pulling out a wire such as the wire 214, allowing the ring 213 to collapse inward, reducing the anchoring pressure.

In some embodiments the device 200 is optionally pulled out of the aorta and/or a patient's body without shrinking into a catheter such as the catheter 216 and/or an introducing catheter.

In some embodiments the device 200 is optionally compressed into a catheter such as the catheter 216 and/or an introducing catheter for removing from the patient's body.

In some embodiments, wires such as Nitinol wires are optionally taken out of the device 200, and then the rest of the device 200 is optionally pulled out of the aorta and/or the patient's body, and/or compressed into a catheter such as the catheter 216 and/or an introducing catheter for removing from the patient's body.

In some embodiments the catheter 216 is optionally advanced toward the mesh 212, and the mesh 212 optionally compressed into the catheter 216, optionally for removing from the patient's body, potentially preventing possible damage to the aortic wall.

Figure 2C:
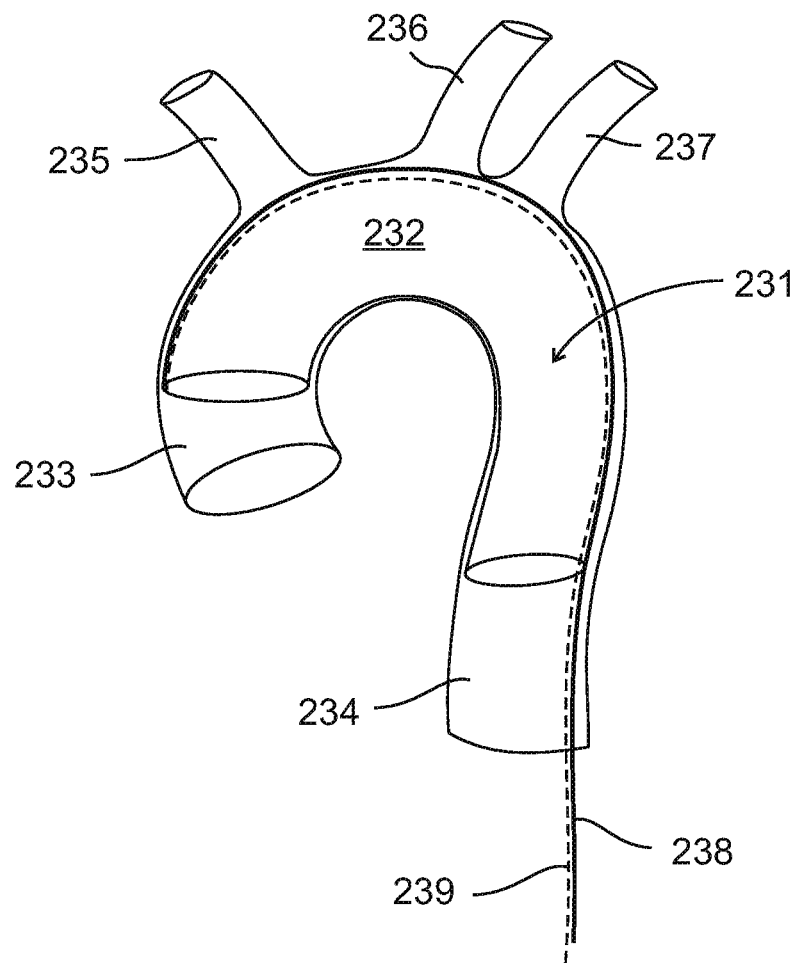
FIG. 2C is a simplified line drawing illustration of a device deployed within an aorta according to an example embodiment of the invention.

Reference is now made to FIG. 2C, which is a simplified line drawing illustration of a device deployed within an aorta according to an example embodiment of the invention.

FIG. 2C shows a section of an aorta, the section extending from a heart-proximal side 233 to a heart-distal side 234, and includes the aortic arch.

FIG. 2C shows a device 231 in the aorta. The device includes a mesh 232 in the aortic arch, and two optional wires 238 239 attached to the mesh 232. The mesh covers artery exits to the brachiocephalic artery 235, the left common carotid artery 236 and the left subclavian artery 237.

The mesh 232 potentially blocks debris flowing with blood in the aorta from entering the above-mentioned arteries.

It is noted that in some embodiments the mesh 232 may optionally extend more or less than shown in FIG. 2C. By way of a non-limiting example the mesh 232 may extend much further on a heart-distal side of aorta, covering more artery exits from the aorta.

In some embodiments the mesh includes pores of approximately 50 microns in diameter.

In some embodiments the mesh 232 is optionally controlled to change its porosity, for example from approximately 50 microns in diameter to a smaller size, providing better protection from debris entering the side arteries.

In some embodiments the mesh 232 is optionally controlled to change its porosity and to completely block blood from entering the side arteries.

In some embodiments the mesh 232 is optionally controlled to change its porosity for a limited amount of time, for example for a few seconds, for example 10 seconds, 30 seconds, 60 seconds, 90 seconds, up to a few minutes, for example two, three, four or five minutes.

In some embodiments the mesh 232 is optionally controlled to change its porosity and to completely block blood from entering the side arteries for a limited amount of time, for example for a few seconds, for example 10 seconds, 30 seconds, 60 seconds, 90 seconds, up to a few minutes, for example two, three, four or five minutes.

Figure 2D:
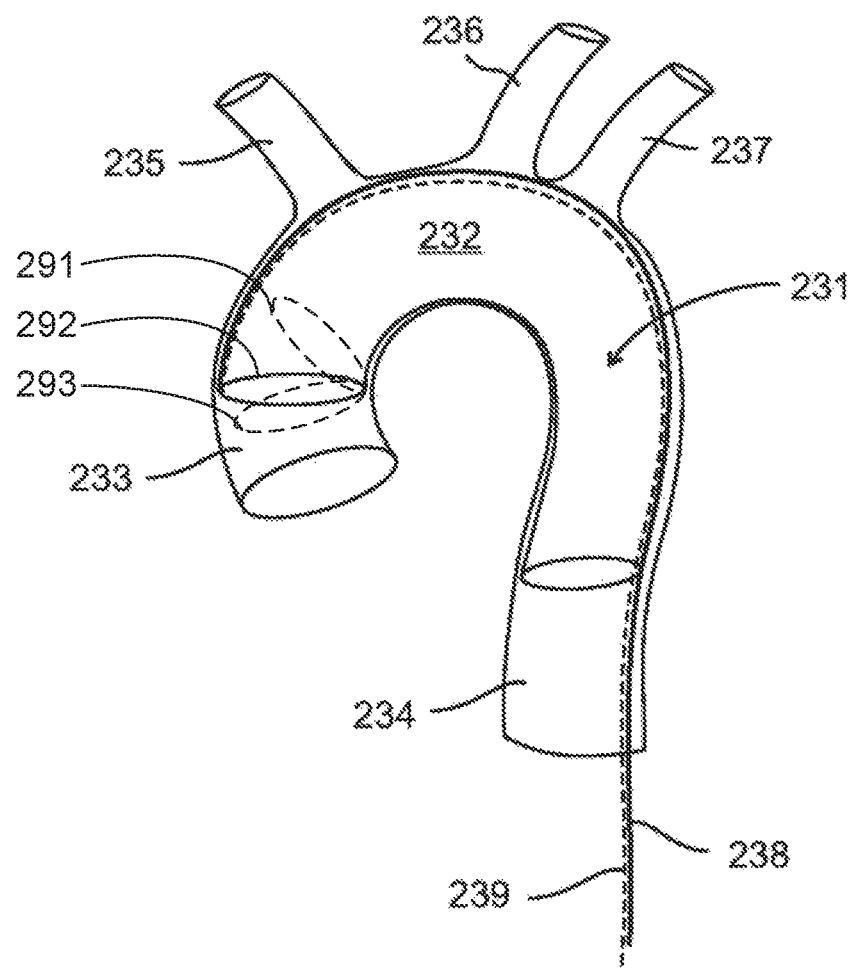
FIG. 2D is a simplified line drawing illustration of a device deployed within an aorta according to an example embodiment of the invention.

Reference is now made to FIG. 2D, which is a simplified line drawing illustration of a device deployed within an aorta according to an example embodiment of the invention.

FIG. 2D shows a section of an aorta, the section extending from a heart-proximal side 233 to a heart-distal side 234, and includes the aortic arch.

FIG. 2D shows a device 231 in the aorta. The device includes a mesh 232 in the aortic arch, and two optional wires 238 239 attached to the mesh 232. The mesh covers artery exits to the brachiocephalic artery 235, the left common carotid artery 236 and the left subclavian artery 237.

It is noted that in some cases, when the device 231 is inserted into the aorta, a heart-proximal end 292 of the device 231 may not be positioned around a circumference of the aorta, and may not prevent blood from flowing around the device 231, between the mesh 232 and walls of the aorta.

FIG. 2D shows two non-limiting examples of the heart-proximal end 292 of the device 231 initially in positions 291 293 which do not prevent blood from flowing around the device 231.

In some embodiments one or more optional wires, such as one or more of the optional wires 238 239, is optionally used to remotely manipulated the heart-proximal end 292 of the device 231 to become properly positioned around a circumference of the aorta, as is shown in the position drawn in FIG. 2D for the heart-proximal end 292 of the device 231.

Figure 2E:
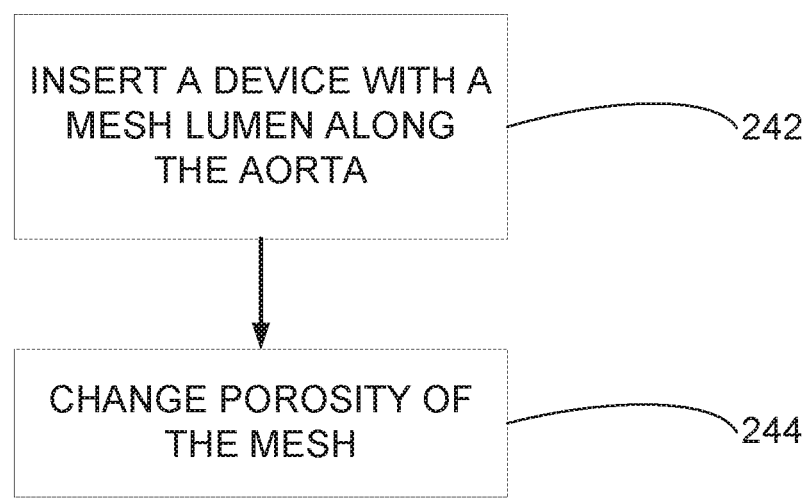
FIG. 2E is a simplified flow chart illustration of a method for protecting side arteries blood-borne debris according to an example embodiment of the invention.

Reference is now made to FIG. 2E, which is a simplified flow chart illustration of a method for protecting side arteries blood-borne debris according to an example embodiment of the invention.

The method of FIG. 2E includes:

inserting a device comprising a first mesh lumen to extend along the aorta (242); and changing porosity of the mesh (244).

In some embodiments the first mesh lumen is shaped and sized to extend along the aorta, from a heart-side of a brachiocephalic artery exit from the aorta to distal of a left subclavian artery exit from the aorta.

In some embodiments the changing porosity is reducing porosity.

Figure 2F:
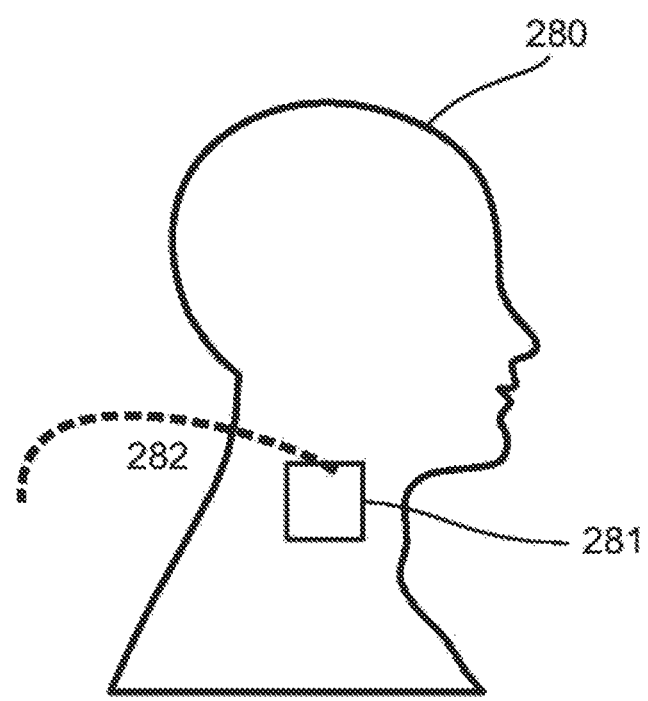
FIG. 2F is a simplified illustration of a device for measuring blood flow to a patient's head according to an example embodiment of the invention.

Reference is now made to FIG. 2F, which is a simplified illustration of a device for measuring blood flow to a patient's head according to an example embodiment of the invention.

In some embodiments, blood flow to a patient's head is affected, by inserting an embodiment of an aortic protection device, and/or by optionally changing porosity of a mesh in the aortic protection device, and/or by optionally performing suction on blood flowing through the patient's aorta and optionally removing the blood from the patient's body.

In some embodiments blood flow to the patient's head is optionally monitored.

FIG. 2F shows a blood flow sensor 281 attached to a patient's head 280.

In some embodiments the blood flow sensor 281 optionally sends 282 blood flow data to a blood flow display.

In some embodiments the blood flow sensor 281 optionally includes a blood flow display.

Figure 2G:
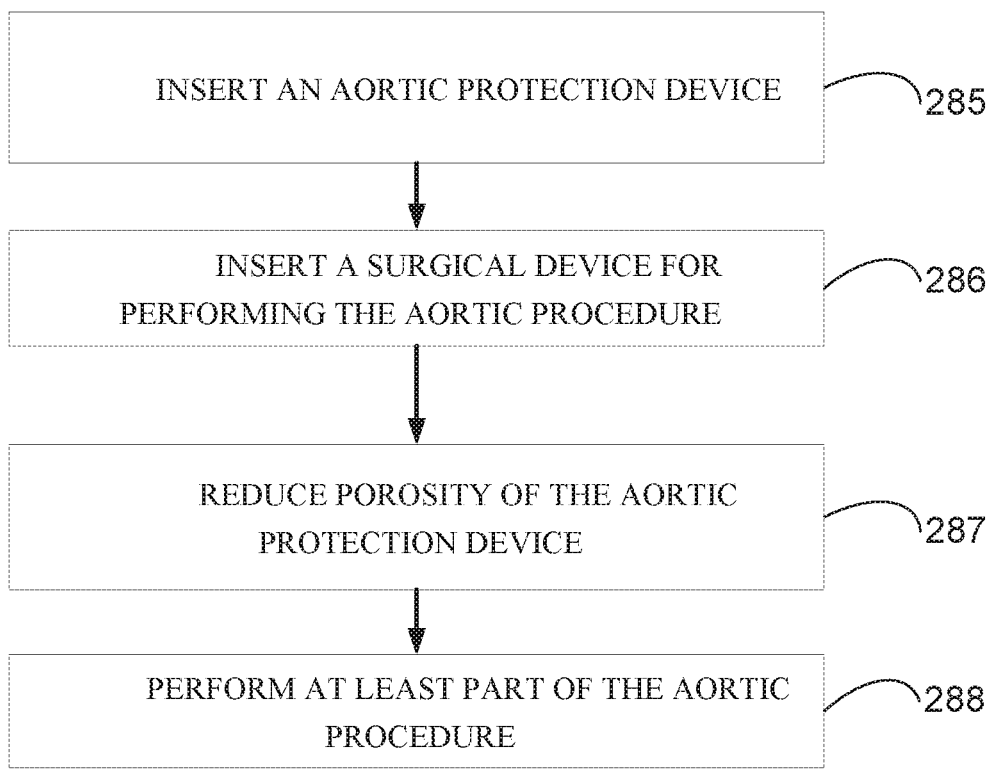
FIG. 2G is a simplified flow chart illustration of a method for protecting cerebral aorta from blood-borne debris during an aortic procedure according to an example embodiment of the invention.

Reference is now made to FIG. 2G, which is a simplified flow chart illustration of a method for protecting cerebral aorta from blood-borne debris during an aortic procedure according to an example embodiment of the invention.

The method of FIG. 2G includes:

inserting an aortic protection device (285). In some embodiments the aortic protection device includes a first mesh lumen shaped and sized to extend along the aorta, from a heart-side of a brachiocephalic artery exit from the aorta to distal of a left subclavian artery exit from the aorta;

inserting a surgical device for performing the aortic procedure (286);

reducing porosity of the aortic protection device (287); and performing at least part of the aortic procedure (288).

In some embodiments reducing the porosity involves decreasing pore size to increase protection of blood flow into side arteries, filtering out even smaller debris from the side arteries, and/or increasing resistance to blood flow to the side arteries.

Figure 2H:
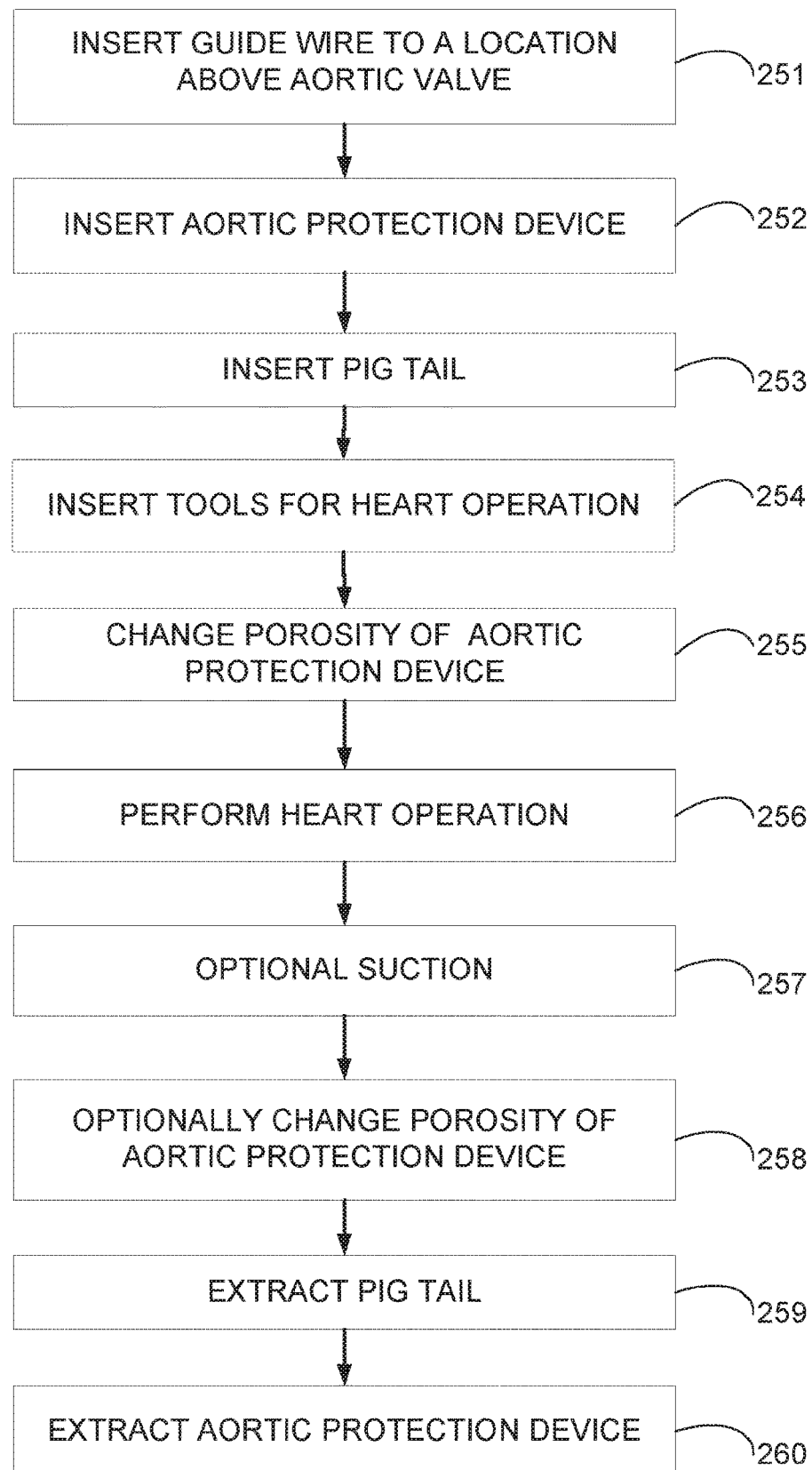
FIG. 2H is a simplified flow chart illustration of a method for protecting side arteries from blood-borne debris according to an example embodiment of the invention.

Reference is now made to FIG. 2H, which is a simplified flow chart illustration of a method for protecting side arteries from blood-borne debris according to an example embodiment of the invention.

FIG. 2H describes an example embodiment and some optional changes in greater detail.

The method of FIG. 2H includes:

Inserting a guide wire to a location above the aortic valve (251).

Inserting an aortic protection device (252).

Optionally using a sheath to insert a pigtail toward the aortic valve (253).

Inserting tools for heart operation (254), in some embodiments optionally through a lumen of the aortic protection device.

Optionally changing porosity of the aortic protection device (255). In some embodiments changing the porosity involves decreasing pore size to increase protection of blood flow into side arteries, filtering out even smaller debris from the side arteries, and/or increasing resistance to blood flow to the side arteries.

Optionally performing the planned heart operation (256), by way of a non-limiting example TAVI.

Optionally, performing suction while the heart operation is performed (257).

Optionally changing porosity of the aortic protection device (258). In some embodiments changing the porosity after a heart operation may involve increasing pore size to increase blood flow into side arteries, or to cease blocking blood from the side arteries.

Optionally extracting the pigtail (259).

Extracting the aortic protection device (260).

In some embodiments the guide wire is optionally inserted through a leg which is opposite a leg planned to be used for a heart operation such as, by way of a non-limiting example, trans-catheter aortic valve implantation (TAVI).

In some embodiments the guide wire serves to guide an aortic protection device sheath, optionally an aortic protection device sheath having a diameter of 8 French. In some embodiments the aortic protection device sheath has a diameter in a range of 6 French to 10 French to 16 French.

In some embodiments the aortic protection device sheath is inserted to approximately 5 centimeters away from the aortic valve. In some embodiments the aortic protection device sheath is inserted to a distance approximately in a range of 2-8 centimeters away from the aortic valve.

In some embodiments inserting the aortic protection device is performed through the aortic protection device sheath.

In some embodiments the inserting the pig tail is performed by inserting a pig tail sheath through the aortic protection device sheath. In some embodiments the inserting the pig tail is intended to include any other tool/guide wire\tube that is inserted for use in a heart procedure.

In some embodiments changing the porosity of the aortic protection device is performed before, optionally just before, optionally a second or a few seconds before, performing the planned heart operation.

In some embodiments changing the porosity is changing from pores sized approximately 200 microns to 100 microns to pores sized approximately 100 to 50 microns.

In some embodiments providing suction to draw blood down the aorta is optionally performed while the heart operation is performed, or even extending after the heart operation is performed, in order to potentially draw blood with debris faster down the aorta, even draw the blood all the way out of the body. In some embodiments the suction is performed through a catheter which is left in the aorta during performance of a heart operation. In some embodiments the suction is performed through a catheter having a diameter of 6, 8, 10 or 12 French.

In some embodiments approximately 30, 60, 80 or 90 cubic centimeters of blood are drawn out of a patient's body during the suction.

In some embodiments changing the porosity after the heart operation is optionally changing from pores sized approximately 75 microns to pores sized approximately 150 microns.

Figure 2I:
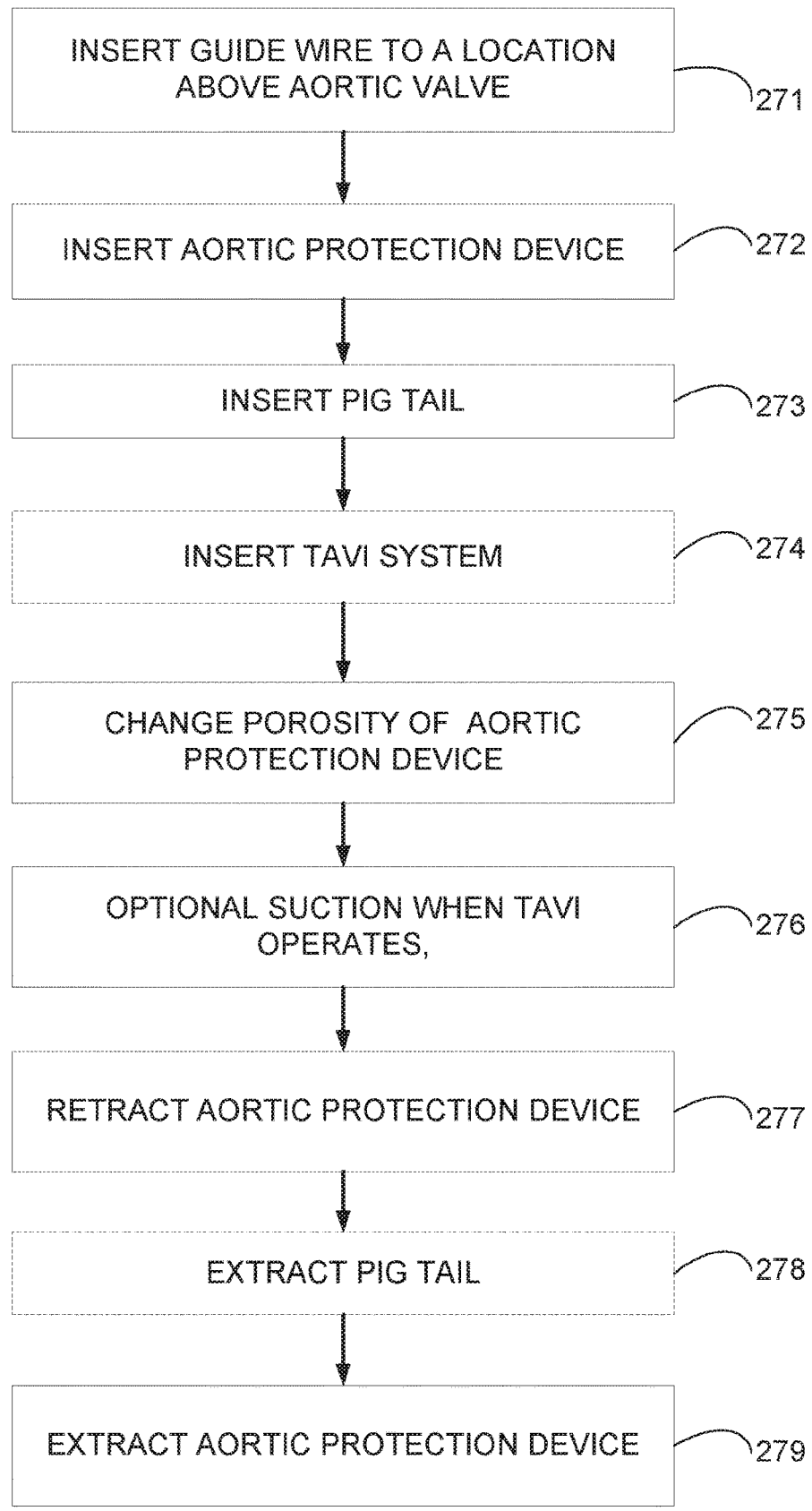
FIG. 2I is a simplified flow chart illustration of a method for protecting side arteries from blood-borne debris according to an example embodiment of the invention.

Reference is now made to FIG. 2I, which is a simplified flow chart illustration of a method for protecting side arteries from blood-borne debris according to an example embodiment of the invention.

FIG. 2I describes an example embodiment and some optional changes in greater detail.

The method of FIG. 2I includes:

Inserting a guide wire to a location above the aortic valve (271).

Inserting an aortic protection device (272).

Optionally inserting a pigtail toward the aortic valve (273).

Optionally inserting tools for heart operation (274), in some embodiments optionally through a lumen of the aortic protection device.

Changing porosity of the aortic protection device (275). In some embodiments changing the porosity involves decreasing pore size to increase protection of blood flow into side arteries, filtering out even smaller debris from the side arteries, and/or increasing resistance to blood flow to the side arteries.

Optionally, performing suction during a period when the heart operation is performed (276).

Optionally, partially retracting the aortic protection device (277) to potentially allow free blood flow to side arteries such as cerebral arteries.

Optionally extracting the pigtail (278).

Extracting the aortic protection device (279).

In some embodiments the guide wire is optionally inserted through a leg which is opposite a leg planned to be used for a heart operation such as, by way of a non-limiting example, trans-catheter aortic valve implantation (TAVI).

In some embodiments the guide wire is optionally inserted to approximately 5 centimeters away from the aortic valve. In some embodiments, the guide wire is optionally inserted to a distance in a range, by way of a non-limiting example, of 2-10 centimeters away from the aortic valve.

In some embodiments inserting the guide wire is performed through an aortic protection device sheath, optionally an aortic protection device sheath having a diameter in a range of 6-10 French.

In some embodiments the inserting the pig tail is performed by inserting a pig tail sheath through the aortic protection device sheath.

In some embodiments changing the porosity of the aortic protection device is performed before, optionally just before, optionally a second or a few seconds before, performing the planned heart operation.

In some embodiments changing the porosity is changing from pores sized approximately 150 microns to pores sized approximately 50-75 microns. In some embodiments changing the porosity is changing from pores sized in a range of 200 to 100 microns to pores sized in a range of 100 to 25 microns.

In some embodiments providing suction to draw blood down the aorta is optionally performed while the heart operation is performed, or even extending after the heart operation is performed, in order to potentially draw blood with debris faster down the aorta, even draw the blood all the way out of the body.

In some embodiments 60-80 cubic centimeters of blood are drawn out of a patient's body during the suction.

In some embodiments the suction is performed between an inner layer and an outer layer of the aortic protection device.

Figure 3A:
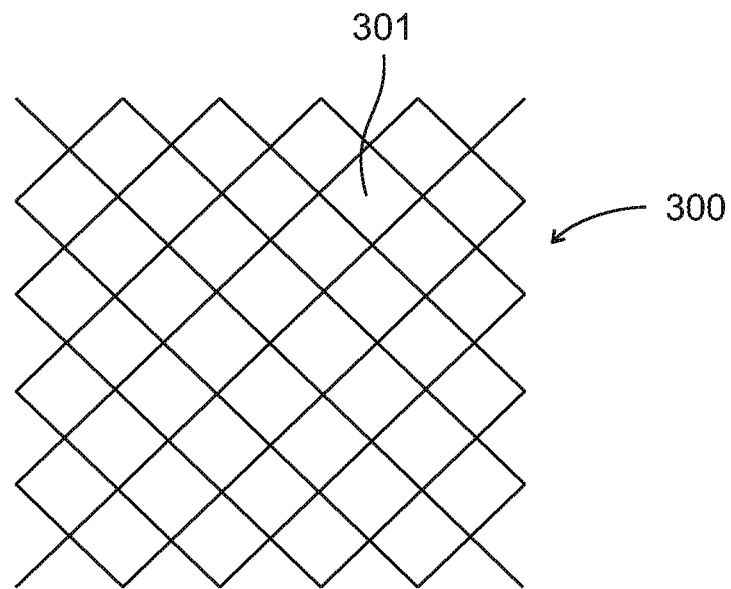
FIG. 3A and 3B are simplified line drawings illustrations of a mesh changing porosity according to an example embodiment of the invention.
Figure 3B:
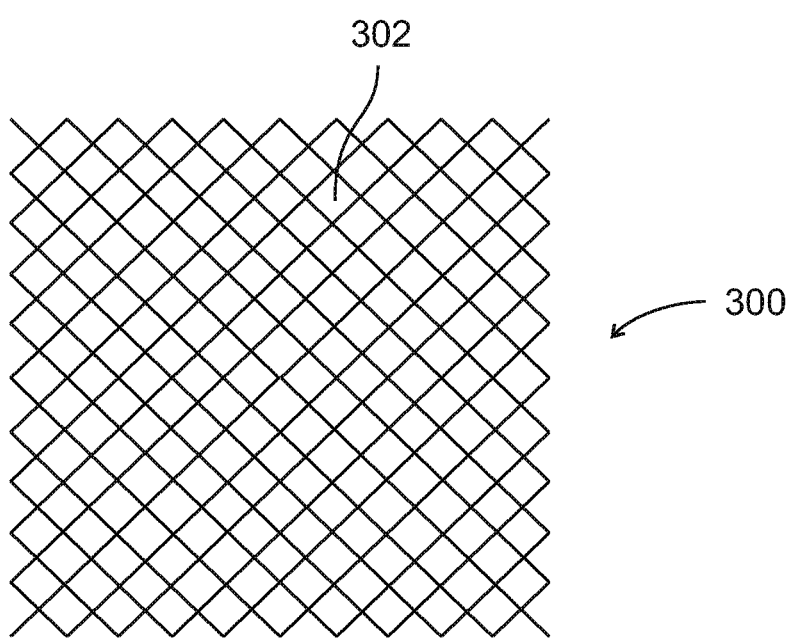

Reference is now made to FIGS. 3A and 3B, which are simplified line drawings illustrations of a mesh changing porosity according to an example embodiment of the invention.

FIG. 3A shows a mesh 300 having a first porosity, and FIG. 3B shows the mesh 300 having a second porosity.

FIG. 3A shows the mesh 300 having larger pores 301 than pores 302 in the mesh 300 of FIG. 3B.

The change in size demonstrated by FIGS. 3A and 3B is intended to show a qualitative change, and is not necessarily drawn to scale.

An example range of pore sizes includes initial large pores in a range of 50 to 200 micron size, and pores and/or meshes and/or aortic protection devices with a changed porosity in a range of 10 to 50 micron size.

Various devices and methods are described herein teaching how to change porosity of a mesh, and/or how to use more than one mesh over a same area to change porosity through the more-than-one meshes.

Figure 4A:
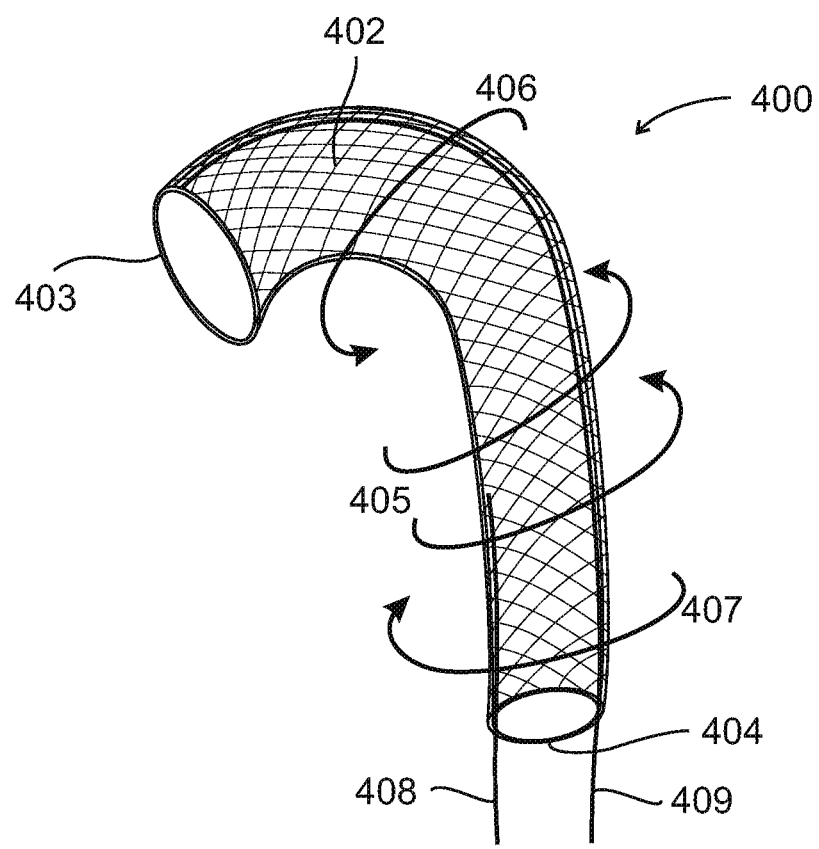
FIG. 4A is a simplified illustration of an aortic protection device configured to change porosity according to an example embodiment of the invention.

Reference is now made to FIG. 4A, which is a simplified illustration of an aortic protection device configured to change porosity according to an example embodiment of the invention.

FIG. 4A shows an aortic protection device 400 including at least one layer of mesh 402.

FIG. 4A also shows a heart-proximal end 403 of the mesh 402 and a heart-distal end 404 of the mesh 402.

In some embodiments one or both of the heart-proximal end 403 of the mesh 402 and the heart-distal end 404 of the mesh 402 optionally include a wire ring attached to the mesh.

In some embodiments the device 400 is optionally connected to one or more control wires.

FIG. 4A shows two control wires: a first control wire 408 and a second control wire 409.

One method of changing porosity of a mesh is to twist the mesh.

FIG. 4A shows the mesh 402 where portions of the mesh 402 are twisted in different directions.

FIG. 4A shows, by way of a non-limiting example, a heart-proximal portion of the mesh 402 twisted toward a first direction 406, a central portion of the mesh 402 twisted toward a, opposite, second direction 405, and a heart-distal portion of the mesh 402 twisted toward a third direction 407.

In some embodiments, a control wire such as the control wire 409 is optionally connected to the mesh 402 at a specific location. For example, the control wire 409 is shown, by way of a non-limiting example, attached to the heart-proximal end 403 of the mesh 402. In some embodiments the control wire may optionally be attached to the above mentioned ring at the heart-proximal end 403 of the mesh 402.

In some embodiments, a control wire such as the control wire 408 is optionally connected to the mesh 402 at a specific location. For example, the control wire 408 is shown, by way of a non-limiting example, attached to the central portion of the mesh 402.

In some embodiments one or more of the control wire(s) 408 409 are optionally twisted in order to twist the mesh 402. In some embodiments the one or more of the control wire(s) 408 409 are wires designed to transfer twist. In some embodiments the one or more of the control wire(s) 408 409 are woven wires, with the weaving pattern designed to transfer twist. In some embodiments the one or more of the control wire(s) 408 409 are solid, non-woven wires designed to transfer twist.

In some embodiments one or more of the control wire(s) 408 409 are optionally twisted in opposite direction. In some embodiments one or more of the control wire(s) 408 409 are optionally twisted in a same direction, by different amounts or angles.

In some embodiments twisting a mesh 402 deployed along an aorta warps a shape of the mesh pores, and the warping potentially changes an open area of the mesh pores.

In some embodiments the heart-proximal end 403 of the mesh 402 optionally expands against side walls of the aorta, potentially anchoring the heart-proximal end 403 of the mesh 402 against rotating with the aorta. In some embodiments a control wire attached to the heart-distal end 404 of the mesh 402 optionally serves to rotate the heart-distal end 404 of the mesh 402 relative to the heart-proximal end 403 of the mesh 402, optionally changing porosity of the mesh 402.

In some embodiments the heart-proximal end 403 of the mesh 402 optionally includes an optional heart-proximal ring (not shown), at a heart-proximal end 403 of the mesh 402, such as the optional heart-proximal ring 213 shown in FIG. 2B. In some embodiments the heart-proximal ring potentially anchors the heart-proximal end 403 of the mesh 402 against side walls of the aorta, potentially preventing rotation. In some embodiments a control wire attached to the heart-distal end 404 of the mesh 402 optionally serves to rotate the heart-distal end 404 of the mesh 402 relative to the heart-proximal end 403 of the mesh 402, optionally changing porosity of the mesh 402.

Figure 4B:
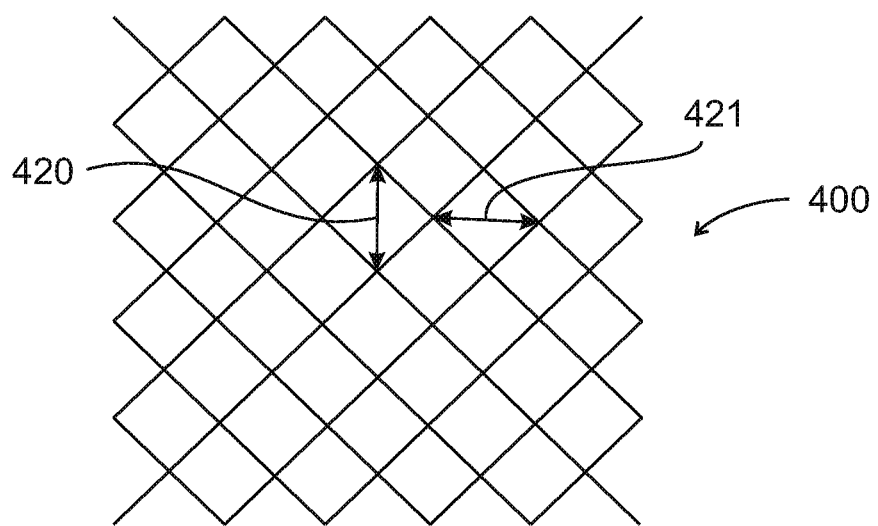
FIGS. 4B, 4C and 4D are simplified line drawings illustrations of a mesh changing porosity according to an example embodiment of the invention.
Figure 4C:
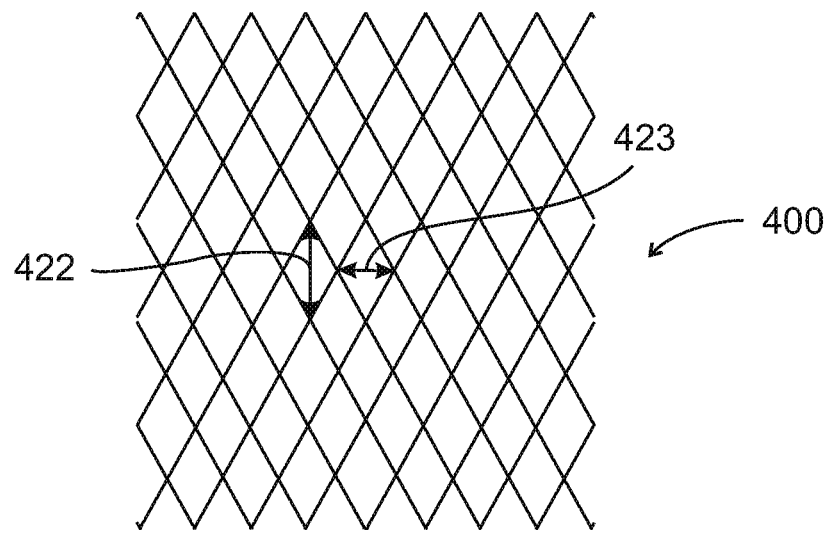
Figure 4D:
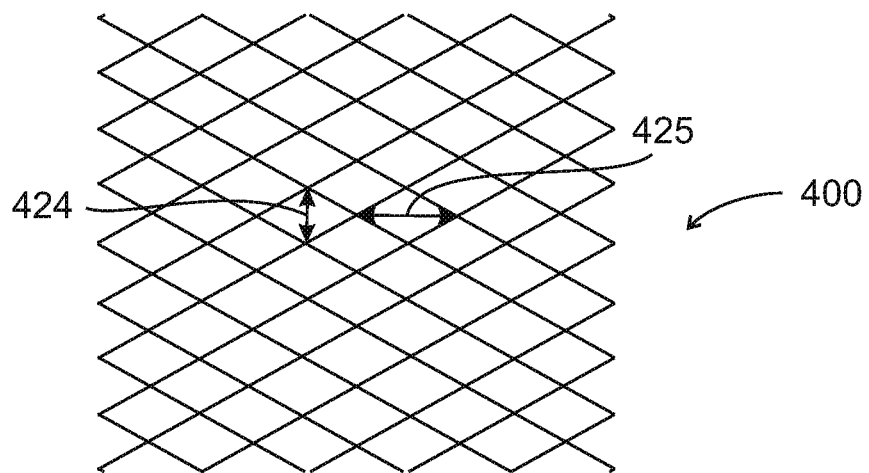

Reference is now made to FIGS. 4B, 4C and 4D, which are simplified line drawings illustrations of a mesh changing porosity according to an example embodiment of the invention.

FIG. 4B shows a mesh 400 having a first porosity. The example embodiment of the mesh 400 of FIG. 4B is drawn as a non-warped shape of the mesh 400.

FIG. 4C shows the mesh 400 warped, optionally by twisting, optionally compressed in a first direction, having a second, different porosity than the porosity of the mesh 400 of FIG. 4B. FIG. 4C shows the mesh 400 presenting smaller mesh pores than the mesh 400 shown in FIG. 4B.

FIG. 4D shows the mesh 400 warped, optionally by twisting, optionally compressed in a second direction, having a different porosity than the porosity of the mesh 400 of FIG. 4B and in some embodiments possibly different than the porosity of the mesh 400 of FIG. 4C. FIG. 4D shows the mesh 400 presenting smaller mesh pores than the mesh 400 shown in FIG. 4B.

In some embodiments the mesh 400 is warped, or the mesh 400 pore sizes are changed, by twisting the mesh 400, optionally around its longitudinal axis. In some embodiments the mesh 400 is warped, or the mesh 400 pore sizes are changed, by changing a length of the mesh 400, optionally by stretching the mesh 400, optionally along its longitudinal axis. In some embodiments the mesh 400 is warped, or the mesh 400 pore sizes are changed, by changing a length of the mesh 400, optionally by shortening or contracting or compressing the mesh 400, optionally along its longitudinal axis.

In some embodiments deploying a device with two layers of mesh along an aorta provides example methods which change a porosity of the device.

FIG. 4B shows a mesh 400 presenting approximately square pores, and FIGS. 4C and 4D show the square mesh holes deforming to a different shape, potentially able to block smaller debris than the pores shown on FIG. 4B. However, in various embodiments the mesh may have holes of other shapes, such as circular, oval, rectangular, rhomboid, and so on. Furthermore, asymmetric shapes may be used, such as, by way of a non-limiting example, shapes not having a mirror symmetry.

Figure 5A:
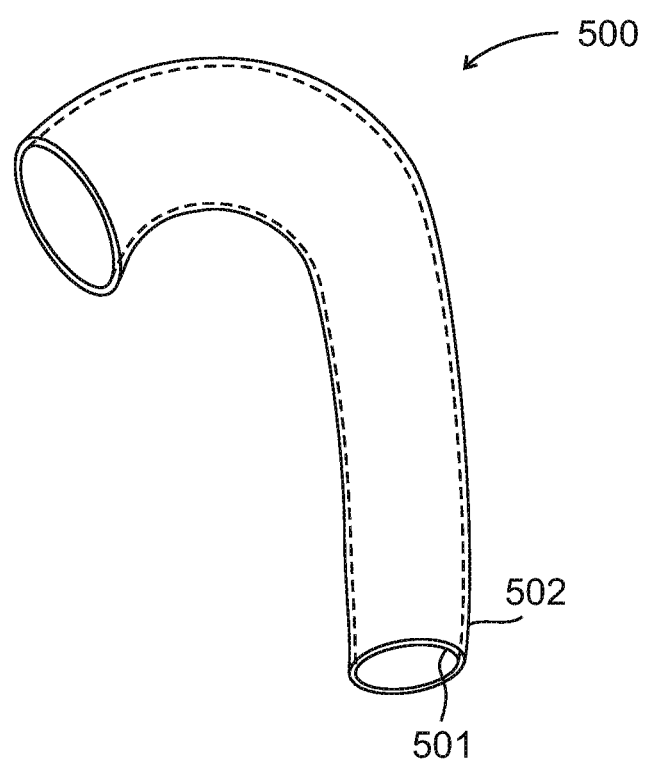
FIG. 5A is a simplified line drawing illustration of aortic protection device according to an example embodiment of the invention.

Reference is now made to FIG. 5A, which is a simplified line drawing illustration of aortic protection device according to an example embodiment of the invention.

FIG. 5A shows an aortic protection device 500 having two layers—an inner layer 501 and an outer layer 502.

In some embodiments both the inner layer 501 and the outer layer 502 are mesh layers having multiple pores, which can potentially block blood-borne debris from passing through the mesh.

In some embodiments the inner layer 501 and the outer layer 502 optionally have pore sizes of 150 microns.

It is noted that wherever pore sizes are mentioned in the specification and claims, the pore size refers to an average diameter of a hole, whether the hole is shaped as a circle, a square, a rectangle, a rhomboid, or some irregular shape.

Figure 5B:
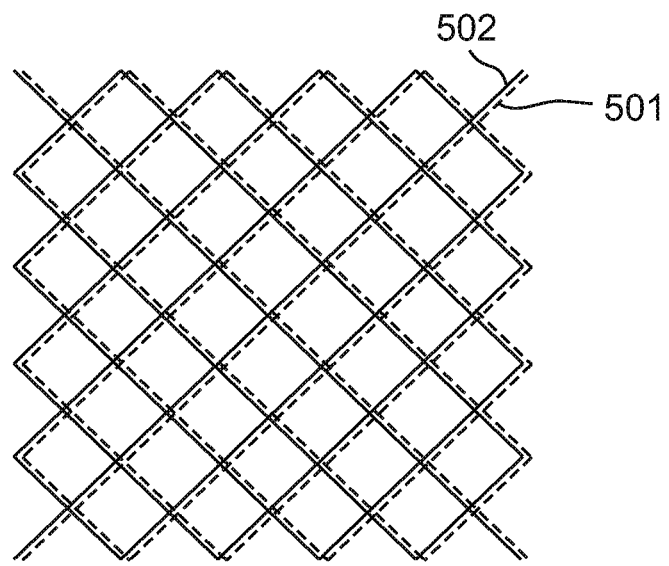
FIGS. 5B and 5C are simplified line drawings illustrations of two layers of mesh presenting different porosities at different times according to an example embodiment of the invention.
Figure 5C:
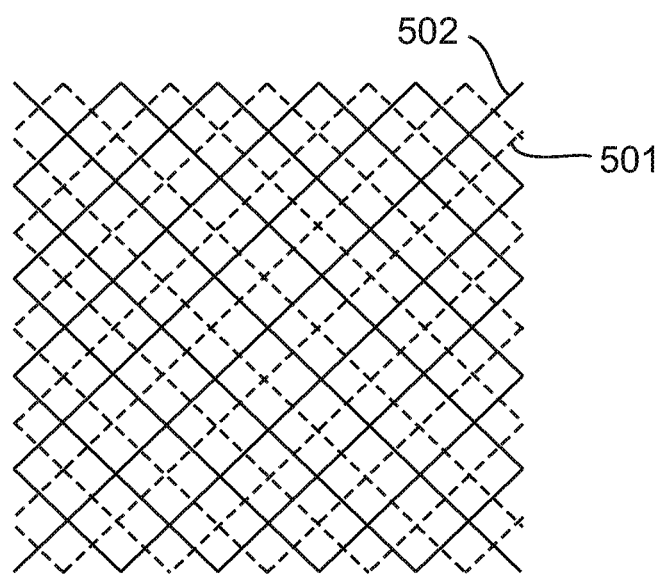

Reference is now made to FIGS. 5B and 5C, which are simplified line drawings illustrations of two layers of mesh presenting different porosities at different times according to an example embodiment of the invention.

FIG. 5B shows a first mesh 501 and a second mesh 502 deployed one behind the other.

In the example embodiments of FIG. 5B the first mesh 501 and the second mesh 502 optionally have mesh pores of approximately a same size.

FIG. 5B illustrates that pores of a combination of the first mesh 501 and the second mesh 502 as shown in FIG. 5B are approximately aligned, FIG. 5B illustrates that a size of debris which would be blocked by the combination of the first mesh 501 and the second mesh 502 as shown in FIG. 5B is approximately similar to a size of debris which would be blocked by a single one of the first mesh 501 and the second mesh 502.

FIG. 5C shows a first mesh 501 and a second mesh 502 deployed one behind the other, with the pore openings shifted and/or twisted relative to each other. By way of a non-limiting example the first mesh 501 and the second mesh 502 are shown with mesh lines and/or intersections in one of first mesh 501 and the second mesh 502 blocking mesh pores in the other one of the first mesh 501 and the second mesh 502.

In some embodiments the first mesh 501 is shifted relative to the second mesh 502. In some embodiments the first mesh 501 is rotated relative to the second mesh 502. In some embodiments the first mesh 501 is twisted relative to the second mesh 502.

The first mesh 501 and the second mesh 502 as deployed in FIG. 5C potentially present much greater blocking of debris, or much lesser porosity.

The two mesh layers deployed as shown in FIG. 5C can potentially serve to present porosity equivalent to a mesh layer with smaller mesh pores than either one of the first mesh 501 and the second mesh 502.

Figure 6A:
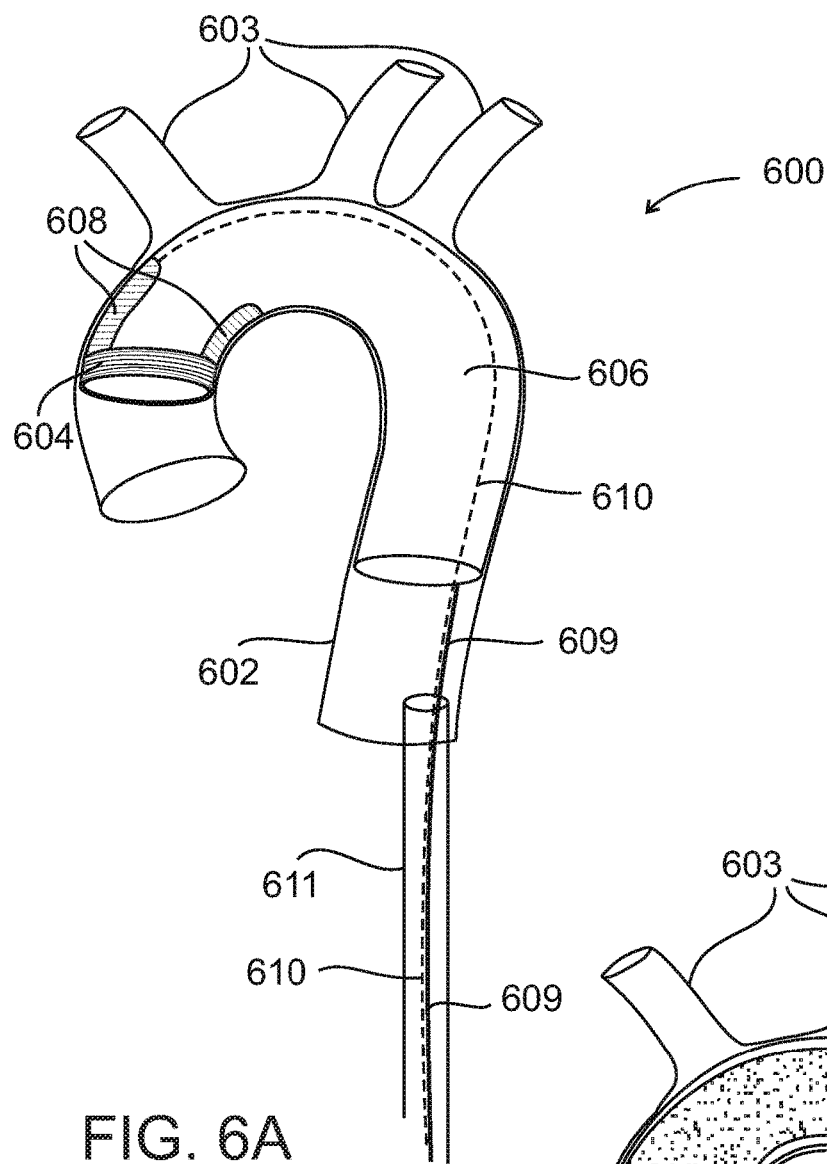
FIGS. 6A and 6B are simplified line drawing illustrations of an aortic protection device according to an example embodiment of the invention.
Figure 6B:
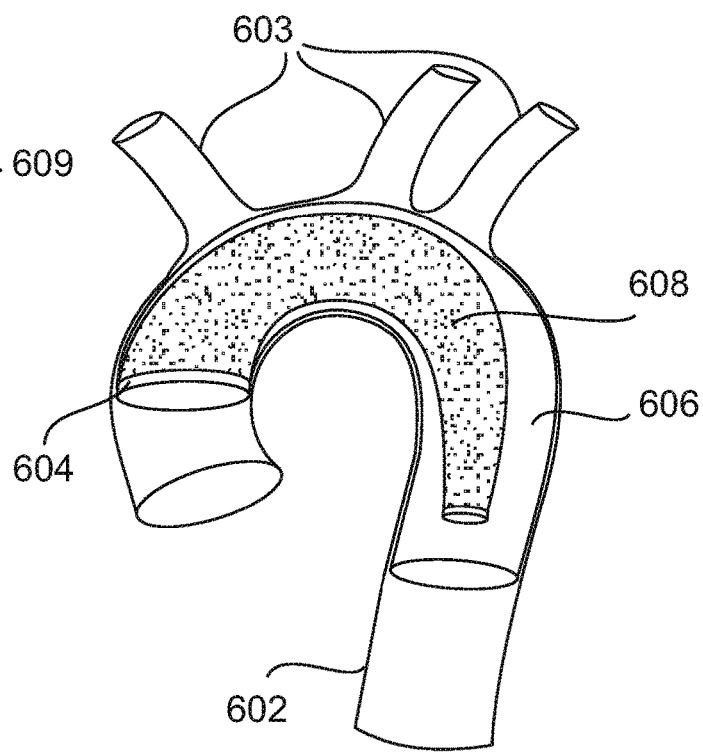

Reference is now made to FIGS. 6A and 6B, which are simplified line drawing illustrations of an aortic protection device according to an example embodiment of the invention.

FIG. 6A shows an aortic protection device 600 deployed in an aorta 602, the aortic protection device 600 having two mesh layers—a first mesh layer 606 and a compactly packed second mesh layer 608.

FIG. 6A also shows an optional ring 604 at a heart-proximal side of the aortic protection device 600, a first control wire 609 attached to a heart-distal end of the device 600, and a second control wire 610 attached to a heart-proximal end of the device 600 and/or to optional ring 604.

FIG. 6A shows the aortic protection device 600 deployed, with the second mesh layer 608 folded or rolled or packaged near the heart-proximal end of the device 600. In such deployment most of the aortic protection device 600 presents a single layer of mesh—the first mesh layer 606. The aortic protection device 600 mostly presents a porosity of the first mesh layer 606.

In some example embodiments the first mesh layer 606 has mesh pores of 175 microns.

FIG. 6B shows the second mesh layer 608 opened and extending along the first mesh layer 606.

In some example embodiments the second mesh layer 608 has mesh pores of 75 microns.

FIG. 6B shows the second mesh layer 608 shorter than the first mesh layer 606. However, FIG. 6B is not intended to limit the relative length of the two mesh layers. In some embodiments the second mesh layer 608 may be shorter than the first mesh layer 606, equal in length to the first mesh layer 606, or longer than the first mesh layer 606.

FIG. 6B shows the second mesh layer 608 extending inside the first mesh layer 606 and not adjacent or touching the first mesh layer 606. However, FIG. 6B is not intended to limit the relative diameter of the two mesh layers. In some embodiments the second mesh layer 608 may extend along and touch the first layer 606, or the second mesh layer 608 may extend along the aorta and inside the first layer 606 yet not touching the first layer 606.

In some embodiments the second mesh layer 608 is optionally shaped to have a larger diameter on a heart-proximal end, and a narrower diameter on a heart-distal end.

In some embodiments the device 600 is deployed before a start of a heart operation. The first mesh layer 606 extends along the aorta 602 and protects side arteries such as side arteries 603 from entry of debris, with a mesh pore size of the first mesh layer 606.

In some embodiments such protection by the first mesh layer 606 optionally blocks larger pieces of debris, and allows blood flow to the side arteries against a resistance of the pores of the first mesh layer 606.

In some embodiments the second mesh layer 608 is deployed before performing a heart operation, especially a heart operation which may potentially dislodge debris, such as TAVI. The second mesh layer provides better protection against debris, potentially blocking smaller pieces of debris, and allows blood flow to the side arteries against a larger resistance, of smaller pores of the second mesh layer 608.

In some embodiments the second mesh layer 608 may potentially block blood flow to the side arteries 603.

In some embodiments the second mesh layer is not a mesh layer with open pores, but a sheet of material, optionally shaped as a lumen, optionally made of flexible material.

Figure 6C:
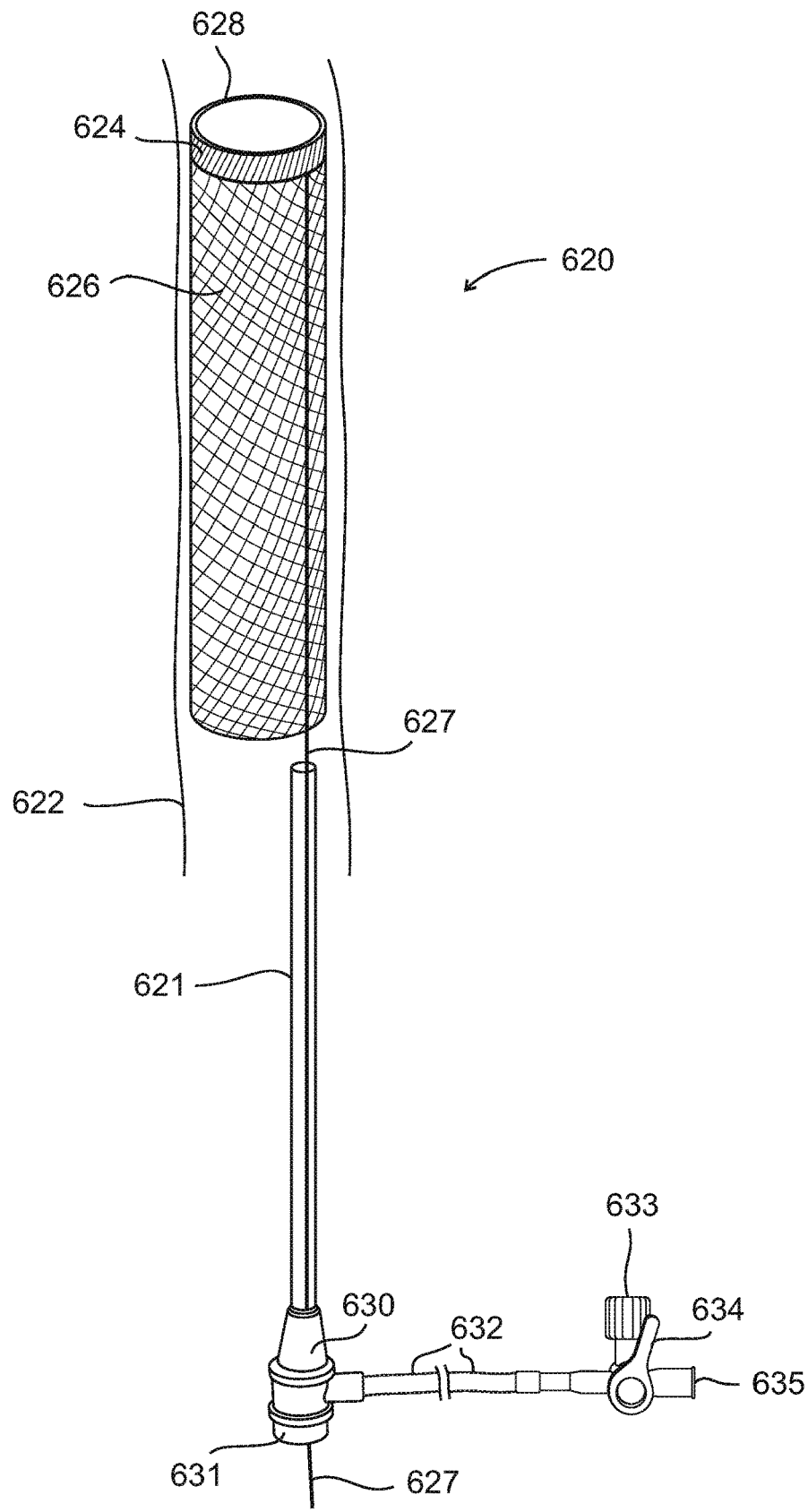
FIG. 6C is a simplified line drawing illustration of an aortic protection device according to an example embodiment of the invention.

Reference is now made to FIG. 6C, which is a simplified line drawing illustration of an aortic protection device according to an example embodiment of the invention.

FIG. 6C shows an aortic protection device 620 deployed in an aorta 622, the aortic protection device 620 having two mesh layers—a first mesh layer 626 and a second mesh layer 624.

In FIG. 6C the aorta is shown as straight. The description of FIG. 6C applies to both a straight section of the aorta 622, for example the descending thoracic aorta and to a curved section of the aorta, such as the aortic arch.

FIG. 6C also shows an optional ring 628 at a heart-proximal side of the aortic protection device 620, and a control wire 627 extending through a catheter 621 and attached to the second mesh layer 624. In some embodiments the control wire 627 is attached to the upper ring 624, and/or a lower ring (not shown) at a heart-distal end of the device 620, and/or along a length of the first mesh layer 626.

FIG. 6C shows the aortic protection device 620 deployed, with the second mesh layer 624 folded or rolled or packaged near the heart-proximal end of the device 620. In such deployment most of the aortic protection device 620 presents a single layer of mesh—the first mesh layer 626. The aortic protection device 620 mostly presents a porosity of the first mesh layer 626.

FIG. 6C also shows a side port 631 at an outside-the-body end of the catheter 621, which enables passing the control wire 627 through the catheter 621 and enables performing suction through a side tube 632. In some embodiments the side tube 632 also includes a valve 634 which controls passage from entrances 633 635 to the side tube 632. In some embodiments one of the entrances 633 635 is optionally connected to low pressure for providing suction of blood though the catheter 621 when the valve 634 is optionally placed in a position which enables connection of suction to the side tube 632.

In some example embodiments the first mesh layer 626 has mesh pores of 175 microns.

In some example embodiments the second mesh layer 624 has mesh pores of 75 microns.

In some embodiments the second mesh layer 624 is deployed by the control wire 627, opened and extended along the first mesh layer 626.

In some embodiments when the second mesh layer 624 is extended along the first layer 626, the device presents a porosity approximately similar to the porosity of the second mesh layer 624.

In some embodiments the second mesh layer 624 is deployed by the control wire 627, which optionally releases a spring which extends the second mesh layer 624 along the first mesh layer 626.

In some embodiments the device 620 is deployed before a start of a heart operation. The first mesh layer 626 extends along the aorta 622 and protects side arteries from entry of debris, with a mesh pore size of the first mesh layer 626.

In some embodiments such protection by the first mesh layer 626 optionally blocks larger pieces of debris, and allows blood flow to the side arteries against a resistance of the pores of the first mesh layer 626.

In some embodiments the second mesh layer 624 is deployed before performing a heart operation, especially a heart operation which may potentially dislodge debris, such as TAVI. The second mesh layer 624 optionally provides better protection against debris, potentially blocking smaller pieces of debris, and allows blood flow to the side arteries against a larger resistance, of smaller pores of the second mesh layer 624.

In some embodiments the second mesh layer 624 may potentially block blood flow to the side arteries.

In some embodiments the second mesh layer is not a mesh layer with open pores, but a sheet of material, optionally shaped as a lumen, optionally made of flexible material.

Figure 6D:
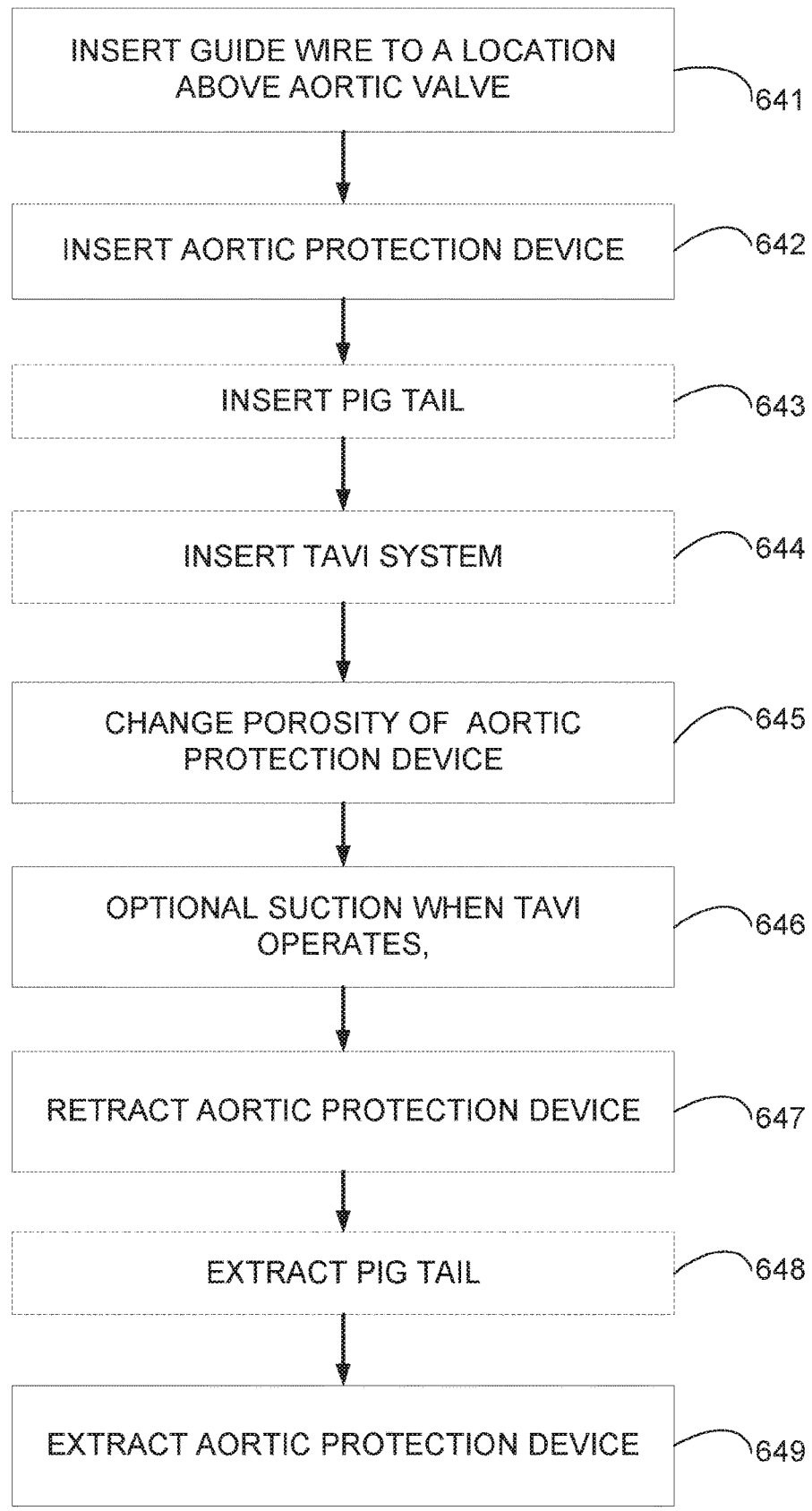
FIG. 6D is a simplified flow chart illustration of a method for protecting side arteries from blood-borne debris according to an example embodiment of the invention.

Reference is now made to FIG. 6D, which is a simplified flow chart illustration of a method for protecting side arteries from blood-borne debris according to an example embodiment of the invention.

The method of FIG. 6D includes:

Inserting a guide wire to a location above the aortic valve (641).

Inserting an aortic protection device (642) which includes a first mesh layer.

Optionally inserting a pigtail toward the aortic valve (643).

Optionally inserting tools for heart operation (644), in some embodiments optionally through a lumen of the aortic protection device.

Changing porosity of the aortic protection device (645). In some embodiments changing the porosity involves deploying a second mesh layer along or covering the first mesh layer.

Optionally, performing suction during a period when the heart operation is performed (646).

Optionally, partially retracting the aortic protection device (647) to potentially allow free blood flow to side arteries such as cerebral arteries.

Optionally extracting the pigtail (648).

Extracting the aortic protection device (649).

In some embodiments changing the porosity of the aortic protection device is performed before, optionally just before, optionally a second or a few seconds before, performing the planned heart operation.

In some embodiments changing the porosity is changing from pores in the first mesh sized approximately 150 microns to pores in the second, additional mesh sized approximately 75 microns.

In some embodiments providing suction to draw blood down the aorta is optionally performed while the heart operation is performed, or even extending after the heart operation is performed, in order to potentially draw blood with debris faster down the aorta, even draw the blood all the way out of the body.

In some embodiments suction is performed through a catheter opening placed near an exit from a lumen of the aortic protection device.

In some embodiments suction is performed through a catheter opening placed within a lumen of the aortic protection device.

In some embodiments 60-80 cubic centimeters of blood are drawn out of a patient's body during the suction.

In some embodiments the suction is performed between the second mesh layer and the first mesh layer of the aortic protection device.

Figure 6E:
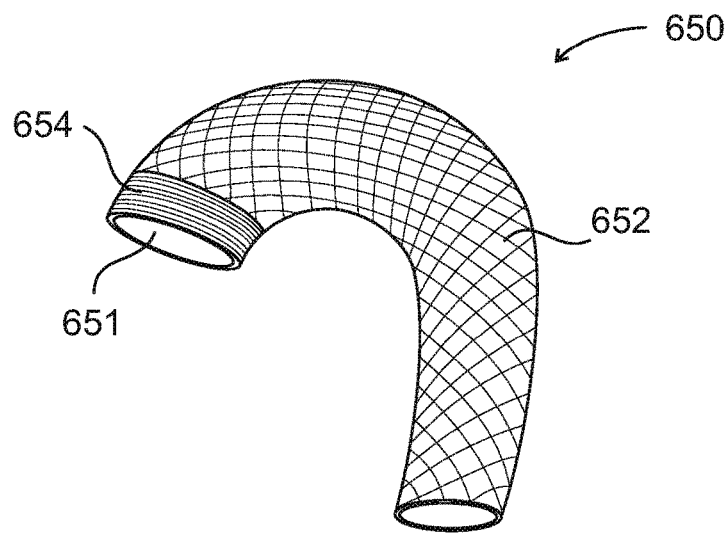
FIGS. 6E and 6F are simplified line drawing illustrations of an aortic protection device according to an example embodiment of the invention.
Figure 6F:
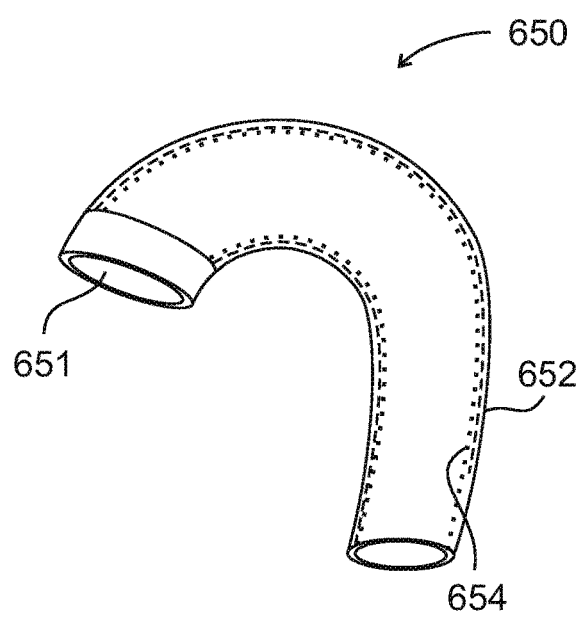

Reference is now made to FIGS. 6E and 6F, which are simplified line drawing illustrations of an aortic protection device according to an example embodiment of the invention.

FIG. 6E shows an aortic protection device 650 in a shape which the aortic protection device 650 assumed when deployed in an aortic arch (not shown), the aortic protection device 650 having two mesh layers—a first mesh layer 652 and a compressed second mesh layer 654 near a heart-proximal end 651 of the device 650.

FIG. 6F shows a cross section of the aortic protection device 650 deployed, with the second mesh layer 654 deployed along the first mesh layer 652.

In some example embodiments the first mesh layer 652 has mesh pores of 175 microns.

In some example embodiments the second mesh layer 654 has mesh pores of 75 microns.

In some embodiments the device 650 is deployed before a start of a heart operation. The first mesh layer 652 extends along the aorta and protects side arteries from entry of debris, with a mesh pore size of the first mesh layer 652.

In some embodiments such protection by the first mesh layer 652 optionally blocks larger pieces of debris, and allows blood flow to the side arteries against a resistance of the pores of the first mesh layer 652.

In some embodiments the second mesh layer 654 is deployed before performing a heart operation, especially a heart operation which may potentially dislodge debris, such as TAVI. The second mesh layer 654 provides better protection against debris, potentially blocking smaller pieces of debris, and allows blood flow to the side arteries against a larger resistance, of smaller pores of the second mesh layer 654.

In some embodiments the second mesh layer 654 may potentially block blood flow to the side arteries.

In some embodiments the second mesh layer is not a mesh layer with open pores, but a sheet of material, optionally shaped as a lumen, optionally made of flexible material.

Figure 6G:
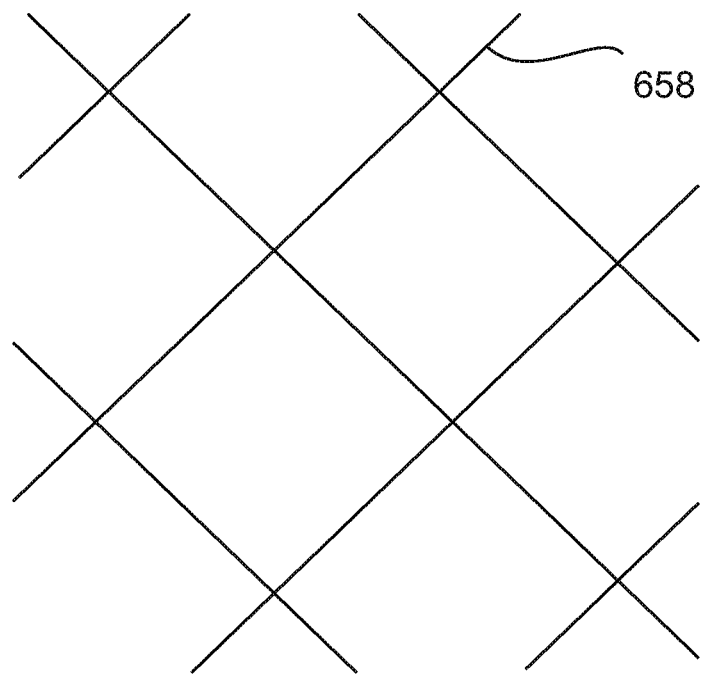
FIGS. 6G and 6H are simplified line drawings illustrations of two layers of mesh presenting different porosities at different times according to an example embodiment of the invention.
Figure 6H:
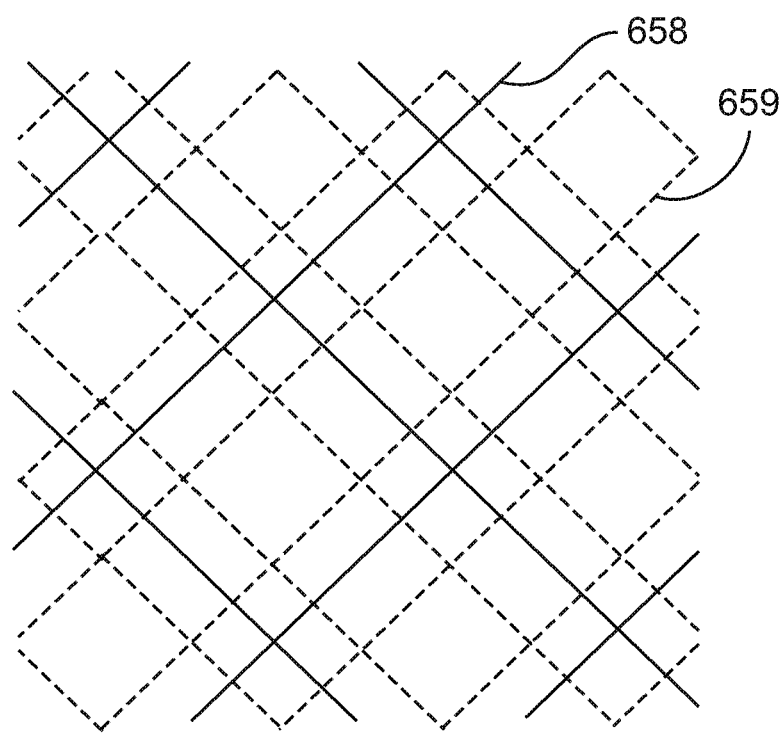

Reference is now made to FIGS. 6G and 6H, which are simplified line drawings illustrations of two layers of mesh presenting different porosities at different times according to an example embodiment of the invention.

FIG. 6G shows a small area in a first mesh layer 658 deployed in an aorta (not shown).

FIG. 6H shows the small area in the first mesh layer 658 with the second mesh layer 659 also deployed. FIG. 6H illustrates that pores of a combination of the first mesh layer 658 and the second mesh layer 659 as shown in FIG. 6H present smaller holes/pores than the first mesh layer 658 alone.

Figure 7A:
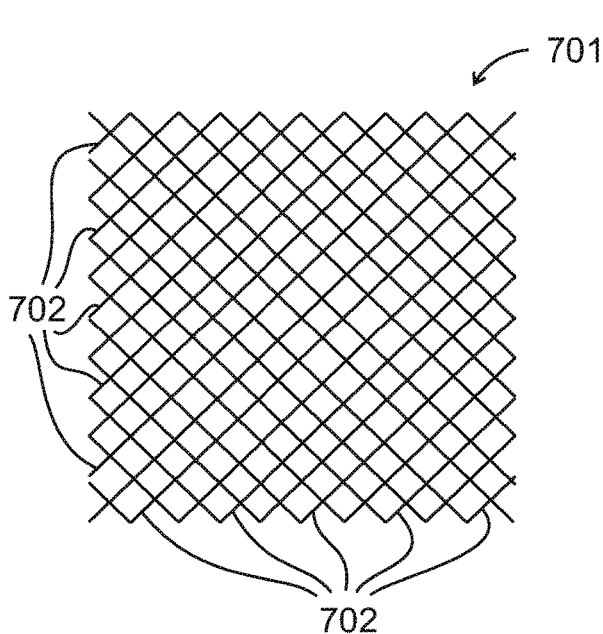
FIGS. 7A and 7B are simplified line drawings illustrations of a mesh presenting different porosities at different times according to an example embodiment of the invention.
Figure 7B:
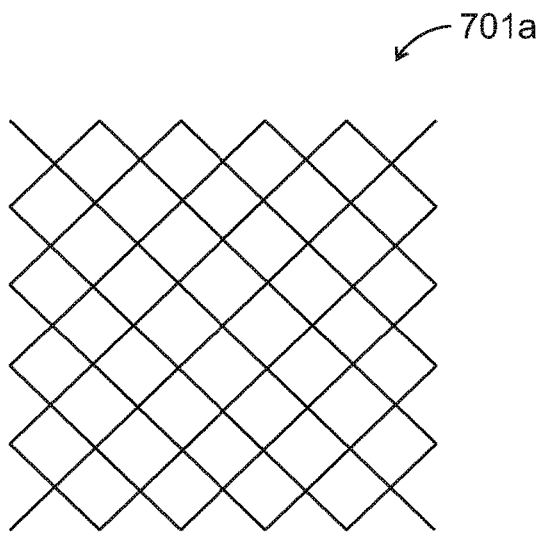

Reference is now made to FIGS. 7A and 7B, which are simplified line drawings illustrations of a mesh presenting different porosities at different times according to an example embodiment of the invention.

FIG. 7A shows a small area in a mesh 701.

FIG. 7B shows the small area in the mesh 701, marked with reference number 701a, where one or more wire(s) or thread(s) 702 from the mesh layer 701 of FIG. 7A have been pulled out of the mesh 701, producing a mesh 701a presenting at least some holes or pores which are larger than the holes or pores of the mesh 701.

Figure 7C:
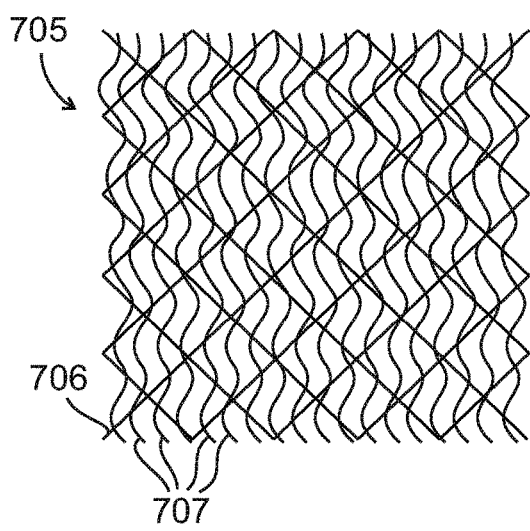
FIGS. 7C and 7D are simplified line drawings illustrations of a mesh presenting different porosities at different times according to an example embodiment of the invention.
Figure 7D:
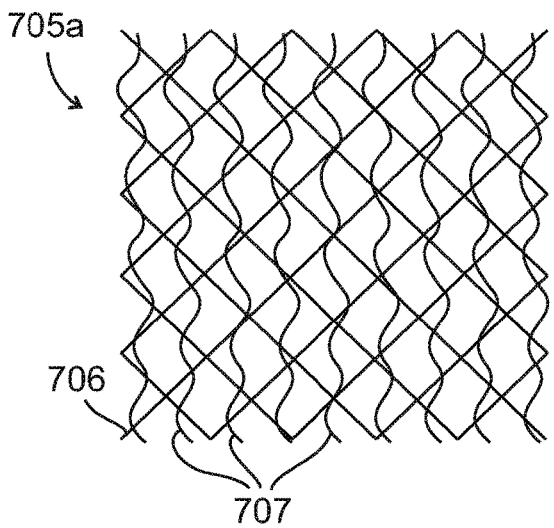

Reference is now made to FIGS. 7C and 7D, which are simplified line drawings illustrations of a mesh presenting different porosities at different times according to an example embodiment of the invention.

FIG. 7C shows a small area in a mesh 705 deployed in an aorta (not shown). The mesh 705 is optionally made of a first set of wires or threads 706, and a second set of wires or threads 707 passing and/or woven through the first set of wires or threads 706. The mesh 705 presents a first pore size.

FIG. 7D shows the small area in the mesh 705, marked with reference number 705*a*, where one or more of the second set of wire(s) or thread(s) 707 have been pulled out of the mesh 705, producing the mesh 705*a* presenting at least some holes or pores which are larger than the holes or pores of the mesh 705.

Figure 7E:
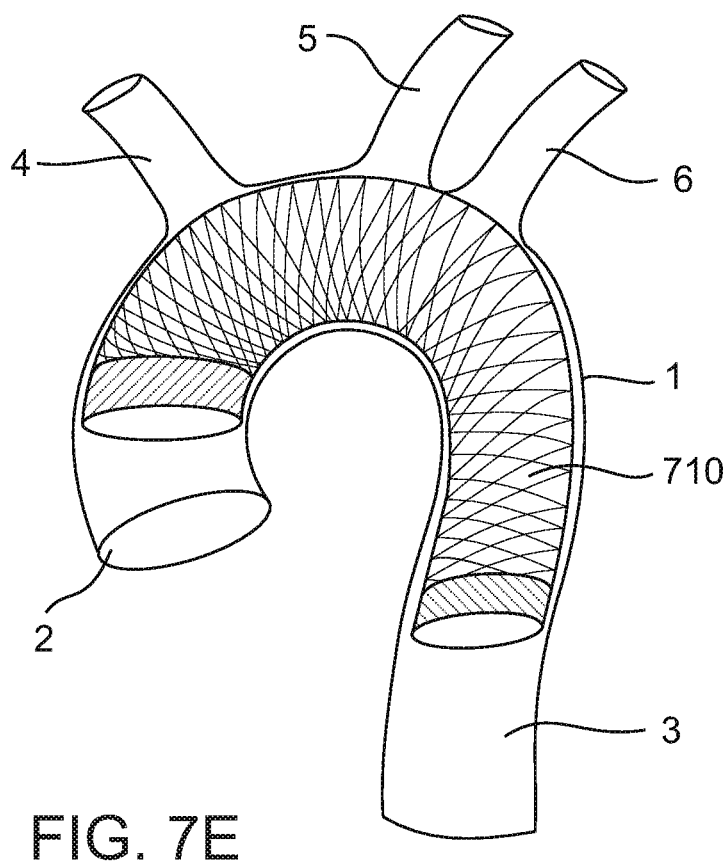
FIG. 7E is a simplified line drawing illustration of an arterial protection device in an aorta according to an example embodiment of the invention.

Reference is now made to FIG. 7E, which is a simplified line drawing illustration of an arterial protection device in an aorta according to an example embodiment of the invention.

FIG. 7E shows a section of an aorta 1. A first end 2 of the section of the aorta 1 is an end near the heart (not shown), and a second end 3 of the section of the aorta 1 is an end more distant from the heart. FIG. 1 shows an aortic arch, and second end 3 corresponds to a descending thoracic aorta.

The section of the aorta 1 is shown with exits to a few major arteries: a first, proximal-to-the-heart exit is to a brachiocephalic artery 4; a second exit is to a left common carotid artery 5; and a third exit is to a left subclavian artery 6.

FIG. 7E shows an example embodiment of an arterial protection device, including a mesh 710, which blocks the exits to the arteries 4, 5, 6.

The mesh 710 presents a first porosity for blocking blood-borne debris.

Figure 7F:
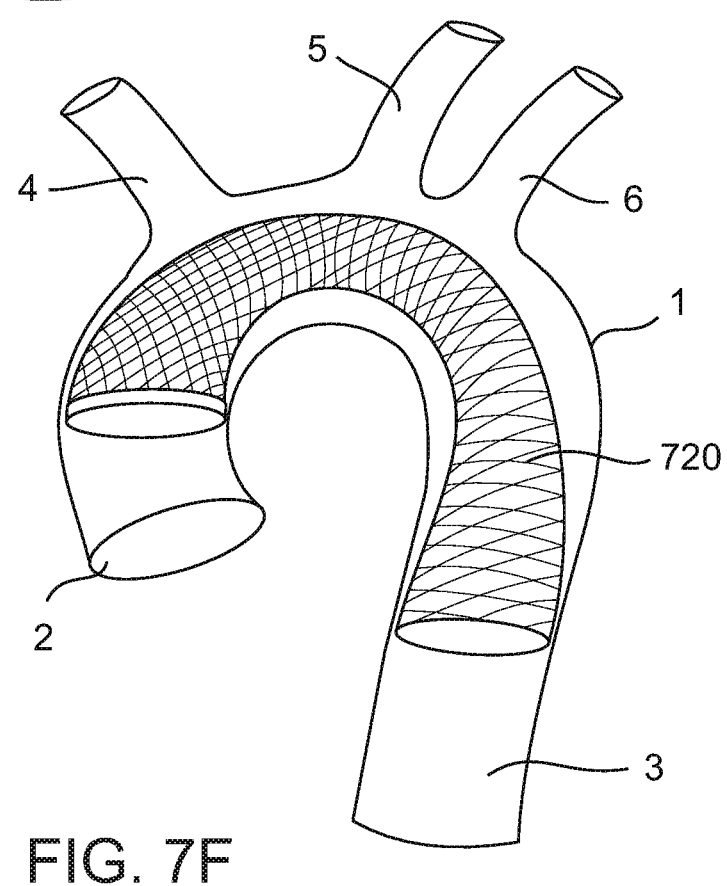
FIG. 7F is a simplified line drawing illustration of the arterial protection device of FIG. 7E, according to an example embodiment of the invention.

Reference is now made to FIG. 7F, which is a simplified line drawing illustration of the arterial protection device of FIG. 7E, according to an example embodiment of the invention.

FIG. 7F shows a mesh 720, corresponding to the mesh 710 of FIG. 7E, after one or more wires have been extracted from the mesh 710.

In some embodiments the mesh 710 contracts after one or more wires have been extracted, and the contraction makes the mesh 720 present smaller pores.

In some embodiments, the mesh 710 of FIG. 7E supports an elastic mesh (not shown) on an outside surface of the mesh 710. In some embodiments, when the mesh 710 contracts to a form of the mesh 720 of FIG. 7F, the elastic mesh on the outside surface of the mesh 720 also contracts, and present smaller pores for blocking blood-borne debris.

In some embodiments the mesh 710 contracts after one or more longitudinal wires have been extracted, and the contraction makes the mesh 720 narrow toward a center of the aorta 1.

Figure 7G:
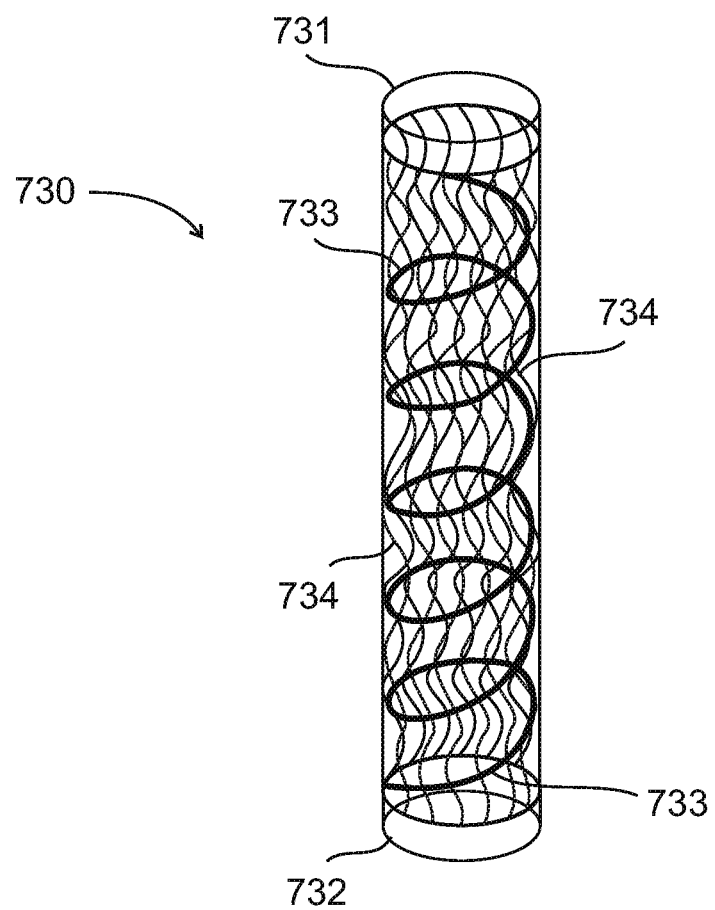
FIG. 7G is a simplified line drawing illustration of an arterial protection device according to an example embodiment of the invention.

Reference is now made to FIG. 7G, which is a simplified line drawing illustration of an arterial protection device according to an example embodiment of the invention.

FIG. 7G shows an arterial protection device 730 with a mesh including one or more permanent wires 733 and one or more additional wires 734 in between the permanent wires 733.

In some embodiments, at least one of the additional wires 734 is pulled out of the mesh, leaving permanent wires 733. In some embodiments the shape of the mesh changes in response to pulling out one or more of the additional wires 734, causing a change in pore sizes of the mesh, and a change in porosity of the arterial protection device 730.

In some embodiments the permanent wires 733 are arranged in a spiral along a length of the arterial protection device 730, and when one or more additional wires 734 are pulled out of the mesh, the spiral permanent wires 733 cause a contraction of a length of the arterial protection device 730, and a decrease in pore size in the mesh.

In some embodiments the arterial protection device 730 optionally includes a first ring 731 at one end of the arterial protection device 730 and optionally includes a second ring 732 at another end of the arterial protection device 730.

In some embodiments the arterial protection device 730 contracts after one or more wires have been extracted, and the contraction makes the arterial protection device 730 present smaller pores.

In some embodiments, the arterial protection device 730 of FIG. 7G supports an elastic mesh (not shown) on an outside surface of the arterial protection device 730. In some embodiments, when the arterial protection device 730 contracts, the elastic mesh on the outside surface of the arterial protection device 730 also contracts, and present smaller pores for blocking blood-borne debris.

In some embodiments the arterial protection device 730 contracts after one or more of the additional wires 734 have been extracted, and the contraction makes the arterial protection device 730 narrow toward a center of the aorta.

Figure 7H:
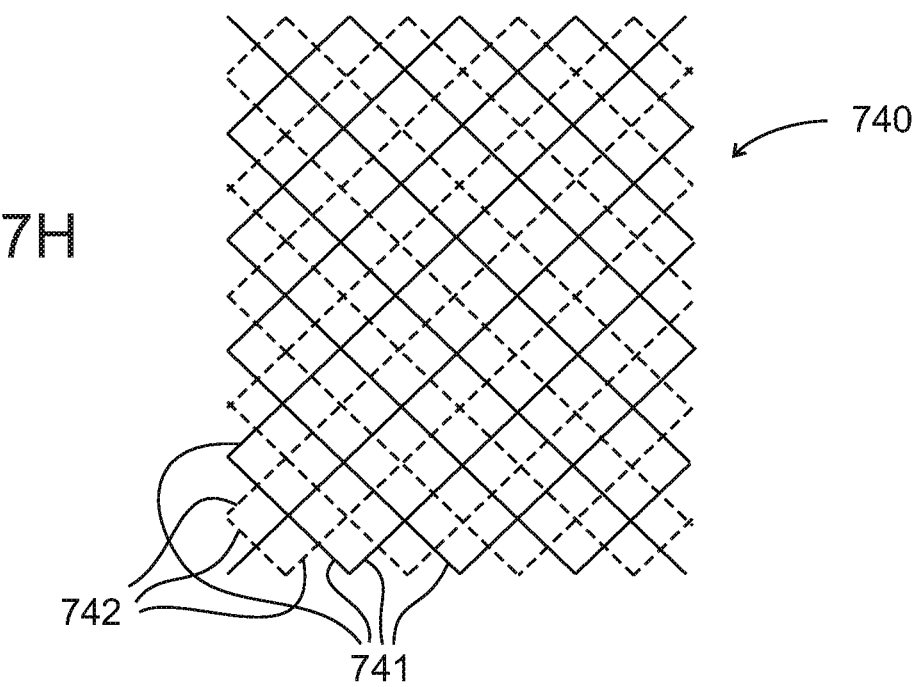
FIG. 7H is a simplified line drawing illustration of a portion of a mesh in an arterial protection device according to an example embodiment of the invention.

Reference is now made to FIG. 7H, which is a simplified line drawing illustration of a portion of a mesh in an arterial protection device according to an example embodiment of the invention.

FIG. 7H shows a mesh including one or more permanent wires 742 and one or more additional wires 741 in between the permanent wires 742.

In some embodiments, at least one of the additional wires 741 is pulled out of the mesh 740, leaving permanent wires 742. In some embodiments the shape of the mesh 740 changes in response to pulling out one or more of the additional wires 741, causing a change in pore sizes of the mesh 740, and a change in porosity of the arterial protection device.

Figure 7I:
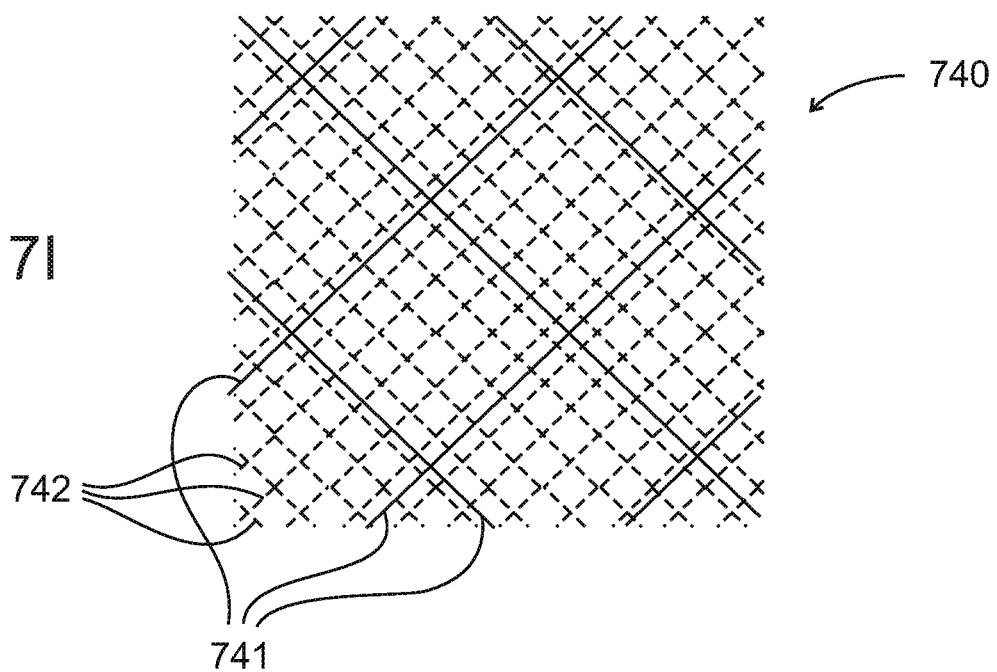
FIG. 7I is a simplified line drawing illustration of the portion of the mesh of FIG. 7H, after at least one of the additional wires was pulled out of the mesh according to an example embodiment of the invention.

Reference is now made to FIG. 7I, which is a simplified line drawing illustration of the portion of the mesh of FIG. 7H, after at least one of the additional wires was pulled out of the mesh according to an example embodiment of the invention.

FIG. 7I shows the mesh 740 of FIG. 7H including one or more permanent wires 742 and one or more additional wires 741 in between the permanent wires 742.

However, some of the additional wires 741 have been pulled out of the mesh 740.

Multi-Layer Aortic Protection Device

An aspect of some embodiments of the invention relates to an aortic protection device which includes more than one layer of mesh.

Properties of meshes described above with reference to embodiments of aortic protection devices are also included in some embodiments of the aortic protection device which include more than one layer of mesh.

Figure 8A:
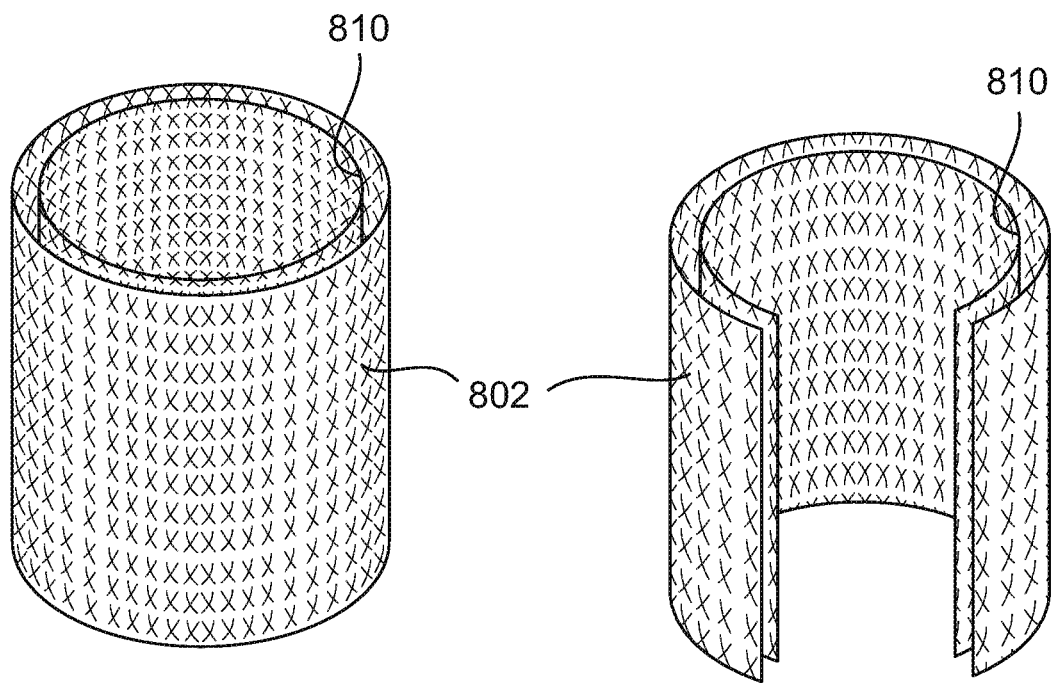
FIG. 8A is a simplified line drawing illustration of a portion of an aortic protection device having two mesh layers according to an example embodiment of the invention.

Reference is now made to FIG. 8A, which is a simplified line drawing illustration of a portion of an aortic protection device having two mesh layers according to an example embodiment of the invention.

FIG. 8A shows a first, inner mesh 801 and a second, outer mesh 802.

In some embodiments the inner mesh 801 includes shape memory material, and provides shape to the aortic protection device, optionally supporting the outer mesh 802 against the outer side of the inner mesh 801. In some embodiments the inner mesh 801 includes shape memory material, and presses the outer mesh 802 against walls of an aorta.

In some embodiments the outer mesh 802 includes a flexible mesh material. In some embodiments the outer mesh 802 includes an elastic mesh material.

In some embodiments the outer mesh 802 includes a polymer material. In some embodiments the outer mesh 802 includes an elastic mesh material.

In some embodiments the outer mesh 802 includes a woven mesh material. In some embodiments the outer mesh 802 includes a woven polymer material. In some embodiments the outer mesh 802 includes a combination of metal mesh and polymer material optionally woven polymer material.

In some embodiments the outer mesh 802 is held stretched against the inner mesh 801.

In some embodiments the outer mesh 802 is loose around the inner mesh 801.

In some embodiments the inner mesh 801 is woven of wires and possesses properties such as the meshes described above with reference to FIGS. 2A-C, 3A-B, 4A-D, 5A-C, 6A-C, 6E-H and 7A-I.

In some embodiments the outer mesh 802 includes shape memory material, and provides shape to the aortic protection device.

In some embodiments the inner mesh 801 includes a flexible mesh material. In some embodiments the inner mesh 801 includes an elastic mesh material.

In some embodiments the inner mesh 801 includes a polymer material. In some embodiments the inner mesh 801 includes an elastic mesh material.

In some embodiments the inner mesh 801 includes a woven mesh material. In some embodiments the inner mesh 801 includes a woven polymer material. In some embodiments the inner mesh 801 includes a combination of metal mesh and polymer material optionally woven polymer material.

In some embodiments the inner mesh 801 is attached to the outer mesh 802.

In some embodiments the inner mesh 801 is loose inside the outer mesh 802.

In some embodiments the outer mesh 802 is woven of wires and possesses properties such as the meshes described above with reference to FIGS. 2A-C, 3A-B, 4A-D, 5A-C, 6A-C, 6E-H and 7A-I.

Figure 8B:
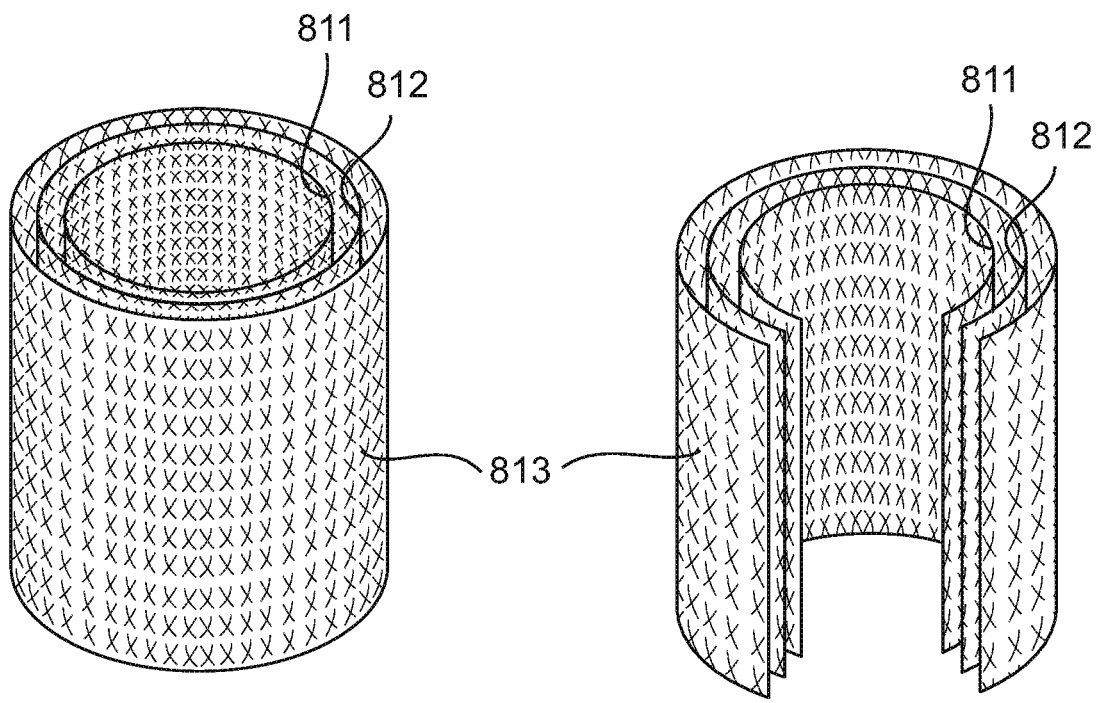
FIG. 8B is a simplified line drawing illustration of a portion of an aortic protection device having three mesh layers according to an example embodiment of the invention.

Reference is now made to FIG. 8B, which is a simplified line drawing illustration of a portion of an aortic protection device having three mesh layers according to an example embodiment of the invention.

FIG. 8B shows a first, inner mesh 811, a second, middle mesh 812 and a third, outer mesh 813.

In some embodiments the inner mesh 811 includes a flexible material such as described above with reference to the flexible material of outer mesh 802 of FIG. 8A.

In some embodiments the middle mesh 812 includes shape memory material such as described above with reference to the shape memory material of inner mesh 801 of FIG. 8A.

In some embodiments the outer mesh 813 includes a flexible material such as described above with reference to the flexible material of outer mesh 802 of FIG. 8A.

Example Embodiments Sealing Entrances of Aortic Branches

Figure 9:
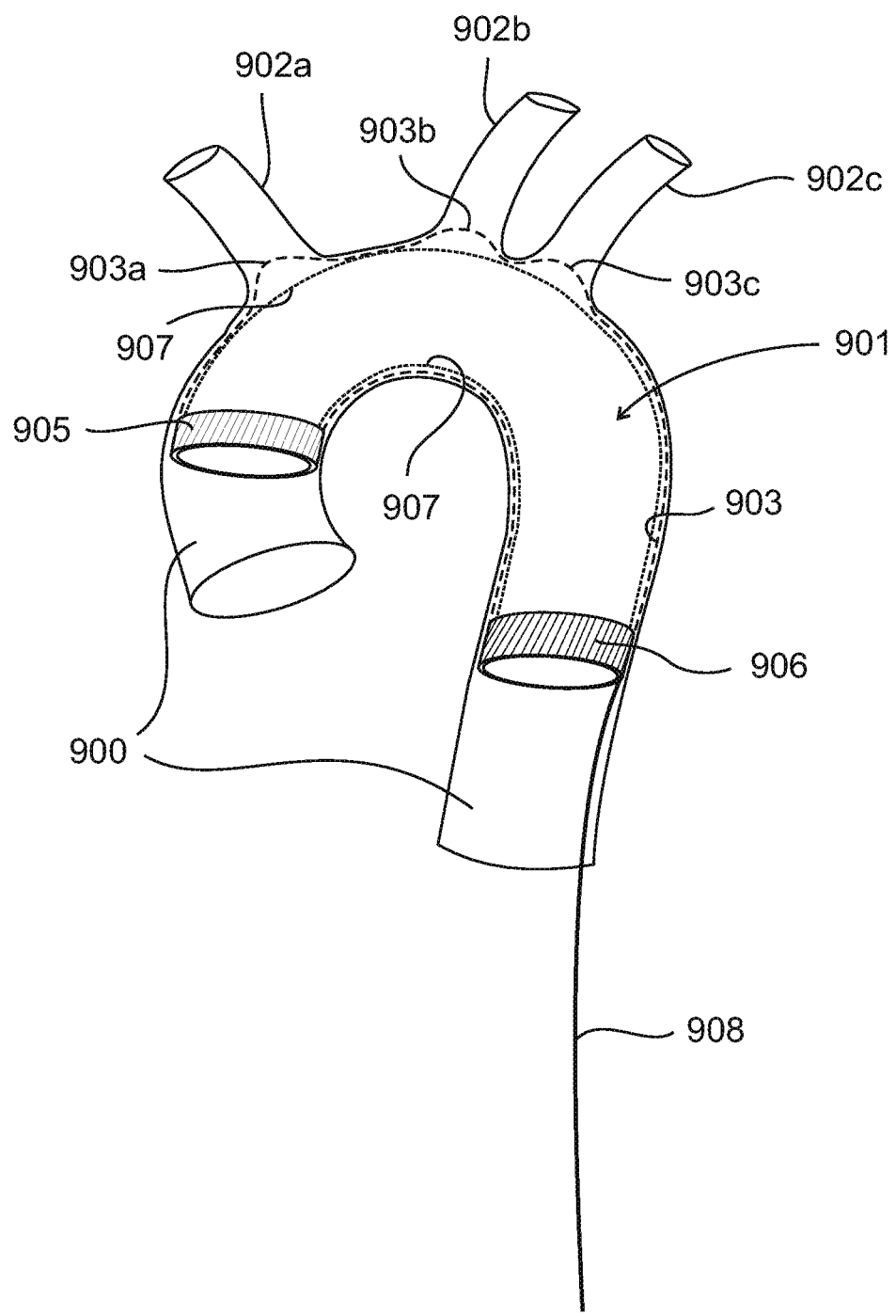
FIG. 9 is a simplified line drawing illustration of an aortic protection device according to an example embodiment of the invention, located in an aorta.

Reference is now made to FIG. 9, which is a simplified line drawing illustration of an aortic protection device according to an example embodiment of the invention, located in an aorta.

FIG. 9 shows an aorta 900, in which an aortic protection device 901 is deployed. The aortic protection device 901 includes a flexible mesh 903, or a flexible outer mesh. Portions 903a 903b 903c of the flexible mesh 903 are optionally swept into aortic branches 902a 902b 902c. The portions 903a 903b 903c f the flexible mesh 903 optionally jut into the aortic branches 902a 902b 902c.

When the portions 903a 903b 903c of the flexible mesh 903 are optionally swept into aortic branches 902a 902b 902c, the portions potentially seal the entrances to the aortic branches 902a 902b 902c.

In some embodiments the aortic protection device 901 includes a flexible outer mesh 903 and an optional inner mesh 907, as described above with reference to FIG. 8A.

In some embodiments the aortic protection device 901 includes three layers of mesh, as described above with reference to FIG. 8B.

In some embodiments the aortic protection device 901 optionally includes an optional ring 905 at a heart-proximal side of the aortic protection device 901. In some embodiments the optional ring 905 is expanded against walls of the aorta 900 optionally anchoring the aortic protection device 901 in the aorta. In some embodiments a length of the optional ring 1005 is in a range of 0.5-3 centimeters.

In some embodiments the aortic protection device 901 optionally includes an optional ring 906 at a heart-distal side of the aortic protection device 901. In some embodiments the optional ring 906 is expanded against walls of the aorta 900 optionally anchoring the aortic protection device 901 in the aorta. In some embodiments a length of the optional ring 1006 is in a range of 0.5-3 centimeters.

In some embodiments the ring 906 at the heart-distal side of the aortic protection device 901 is optionally closed before retrieval of the aortic protection device 901, potentially closing a downstream exit of the aortic protection device 901, preventing debris from flowing downstream of the aortic protection device 901.

In some embodiments the ring 905 at the heart-proximal side of the aortic protection device 901 is optionally closed before retrieval of the aortic protection device 901, potentially closing an exit from the aortic protection device 901, trapping debris inside the aortic protection device 901, potentially enabling withdrawing the debris together with the aortic protection device 901 from a patient's body.

In some embodiments the aortic protection device 901 is optionally attached to a control wire 908 during deployment.

Example Embodiments of Speeding Up Blood Flow in Aorta

Figure 10A:
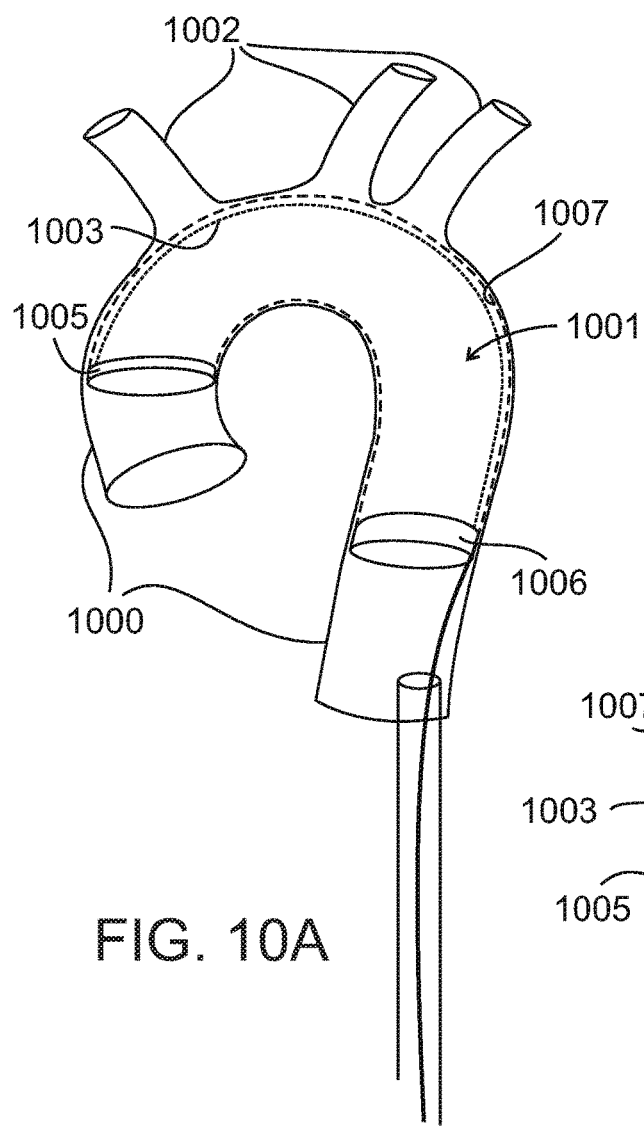
FIGS. 10A and 10B are simplified line drawing illustrations of an aortic protection device according to an example embodiment of the invention, located in an aorta.
Figure 10B:
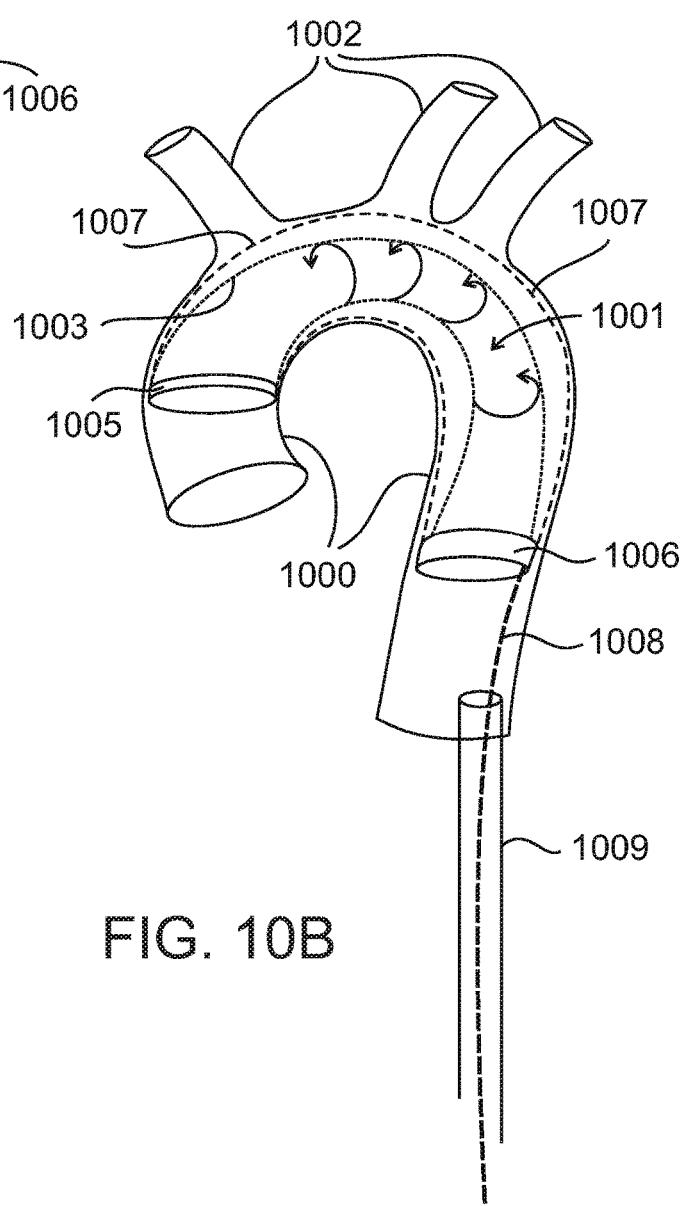

Reference is now made to FIGS. 10A and 10B, which are simplified line drawing illustrations of an aortic protection device according to an example embodiment of the invention, located in an aorta.

FIGS. 10A and 10B show how the aortic protection device is optionally used, in some embodiments, to speed up blood flow along the aorta, potentially sweeping away debris and potentially lowering a probability that the debris block an artery branching off the aorta.

FIGS. 10A and 10B show an aorta 1000, in which an aortic protection device 1001 is deployed. The aortic protection device 1001 includes a flexible mesh 1003, or a flexible inner mesh 1003. FIGS. 10A and 10B also show aortic branches 1002.

FIG. 10A shows the aortic protection device 1001 with the flexible mesh 1003 deployed along the walls of the aorta 1000.

In some embodiments deployment of the aortic protection device 1001 as shown in FIG. 10A is performed before surgical operation on the heart or heart valve, such as TAVI, are performed, so before debris is potentially dislodged from the heart or heart valve.

FIG. 10B shows the flexible mesh 1003 reshaped as a narrower lumen, for example as described above with reference to FIG. 6B and/or FIG. 7F. In some embodiments, when the flexible mesh 1003 is reshaped as a narrower lumen, blood flows faster along the narrower lumen, potentially sweeping away debris and potentially lowering a probability that the debris block an artery branching off the aorta. In some embodiments, when the flexible mesh 1003 is reshaped as a narrower lumen, mesh holes in the narrower lumen contract, we smaller, potentially blocking smaller pieces of debris from passing through the mesh. In some embodiments the flexible mesh 1003 is reshaped as a narrower lumen just before and/or during a time when surgical operation on the heart or heart valve, such as TAVI, is performed, so as to potentially sweep away debris and potentially lower a probability that the debris block an artery branching off the aorta, and/or to block smaller pieces of debris from passing through the mesh 1003.

FIGS. 10A and 10B also show a catheter 1009 and a control wire 1008, optionally used for controlling the narrowing of the lumen of the flexible mesh 1003.

In some embodiments the aortic protection device 1001 optionally includes an optional ring 1005 at a heart-proximal side of the aortic protection device 1001. In some embodiments the optional ring 1005 is expanded against walls of the aorta 1000 optionally anchoring the aortic protection device 1001 in the aorta. In some embodiments the optional ring 1005 remains expanded against walls of the aorta 1000 even when the lumen of the flexible mesh 1003 is made narrow, optionally anchoring the aortic protection device 1001 in the aorta.

In some embodiments the aortic protection device 1001 optionally includes an optional ring 1006 at a heart-distal side of the aortic protection device 1001. In some embodiments the optional ring 1006 is expanded against walls of the aorta 1000 optionally anchoring the aortic protection device 1001 in the aorta. In some embodiments the optional ring 1006 remains expanded against walls of the aorta 1000 even when the lumen of the flexible mesh 1003 is made narrow, optionally anchoring the aortic protection device 1001 in the aorta.

In some embodiments the aortic protection device 1001 includes a flexible outer mesh and an additional inner mesh, as described above with reference to FIG. 8A.

In some embodiments the aortic protection device 1001 includes three layers of mesh, as described above with reference to FIG. 8B.

Example Embodiments of Retrieval of an Aortic Protection Device

Figure 11:
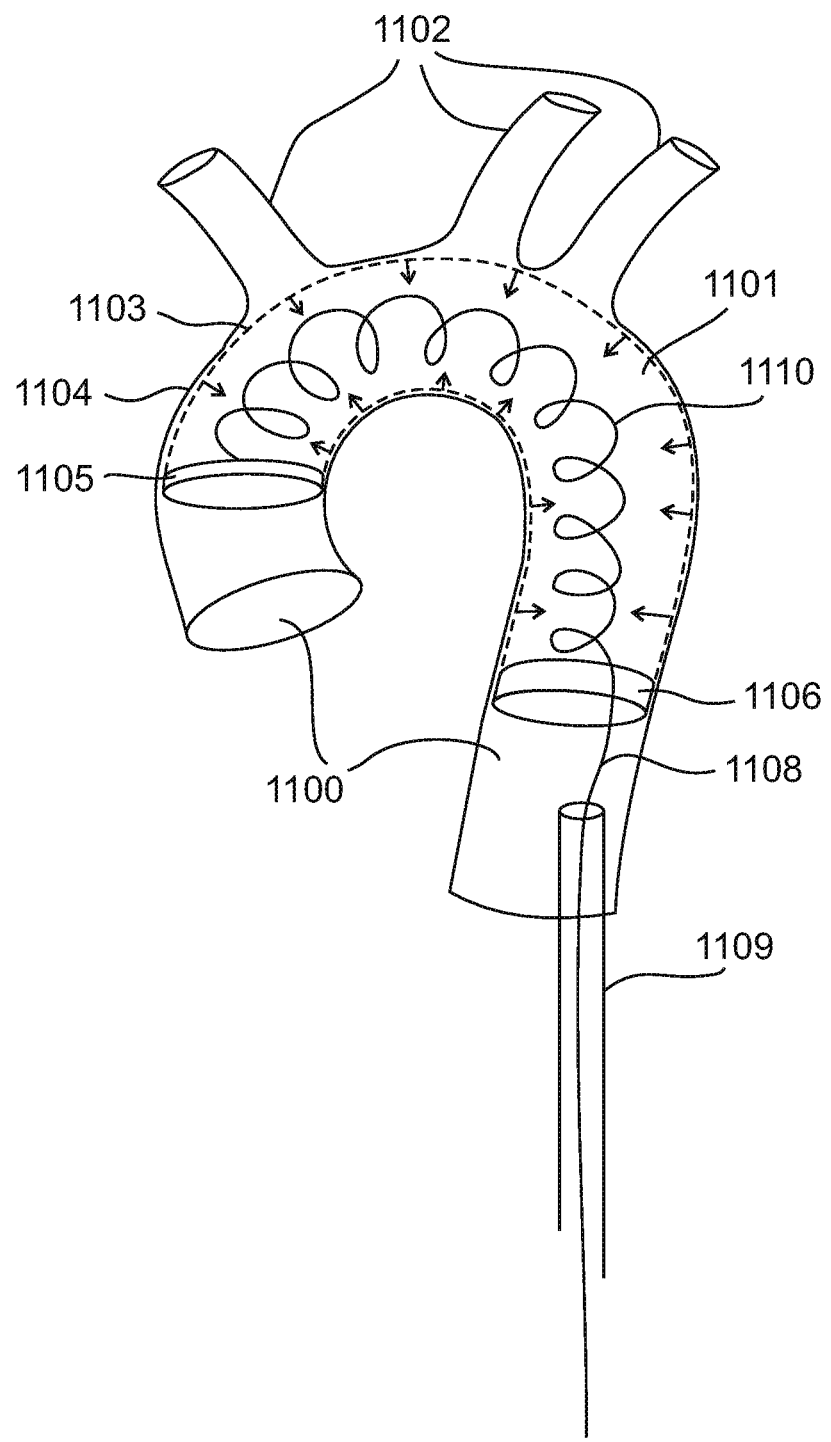
FIG. 11 is a simplified line drawing illustration of an aortic protection device according to an example embodiment of the invention, located in an aorta.

Reference is now made to FIG. 11, which is a simplified line drawing illustration of an aortic protection device according to an example embodiment of the invention, located in an aorta.

FIG. 11 shows an aorta 1100, in which an aortic protection device 1101 is deployed. The aortic protection device 1101 includes a flexible mesh 1103. FIG. 11 also shows aortic branches 1102.

FIG. 11 will be used to describe example embodiments of a process of extracting the aortic protection device 1101 after deployment and optionally after a heart operation such as TAVI.

First, some optional components of the aortic protection device 1101 are described.

In some embodiments the aortic protection device 1101 includes a flexible outer mesh 1103 and an optional inner mesh, as described above with reference to FIG. 8A.

In some embodiments the aortic protection device 1101 includes three layers of mesh, as described above with reference to FIG. 8B.

In some embodiments the aortic protection device 1101 optionally includes an optional ring 1105 at a heart-proximal side of the aortic protection device 1101.

In some embodiments the aortic protection device 1101 optionally includes an optional ring 1106 at a heart-distal side of the aortic protection device 901.

In some embodiments the aortic protection device 901 is optionally attached to a control wire 1108 and a catheter 1109 during deployment.

Next, a first example embodiment of a process for retrieval of the aortic protection device 1101 is described.

In some embodiments the retrieval is optionally performed after heart surgery and/or TAVI and/or after the aortic protection device 1101 has been placed in high filtration mode, with mesh pores of the aortic protection device 1101 smaller than when initially deployed.

In some embodiments, the aortic protection device 1101 is rotated so that an external wall of the aortic protection device 1101 slides rotationally along walls of the aorta 1100. The rotation of the aortic protection device 1101 relative to the walls of the aorta potentially reduces adhesion of the aortic protection device 1101 to the walls of the aorta. Following the rotation the aortic protection device 1101 is optionally pulled into the catheter 1109 or into another catheter (not shown) specifically intended for retrieval of the aortic protection device 1101.

In some embodiments the aortic protection device 1101 is rotated gradually, from a heart-proximal end to a heart-distal end. Such gradual rotation potentially encourages debris to move away from the heart-proximal end of the aortic protection device 1101.

In some embodiments shape memory wires 1110 which are part of the aortic protection device 1101 are optionally pulled out of the aortic protection device 1101, reducing pressure of the mesh against walls of the aorta, following which a rest of the aortic protection device 1101 is pulled into a catheter for retrieving the aortic protection device 1101.

Figure 12:
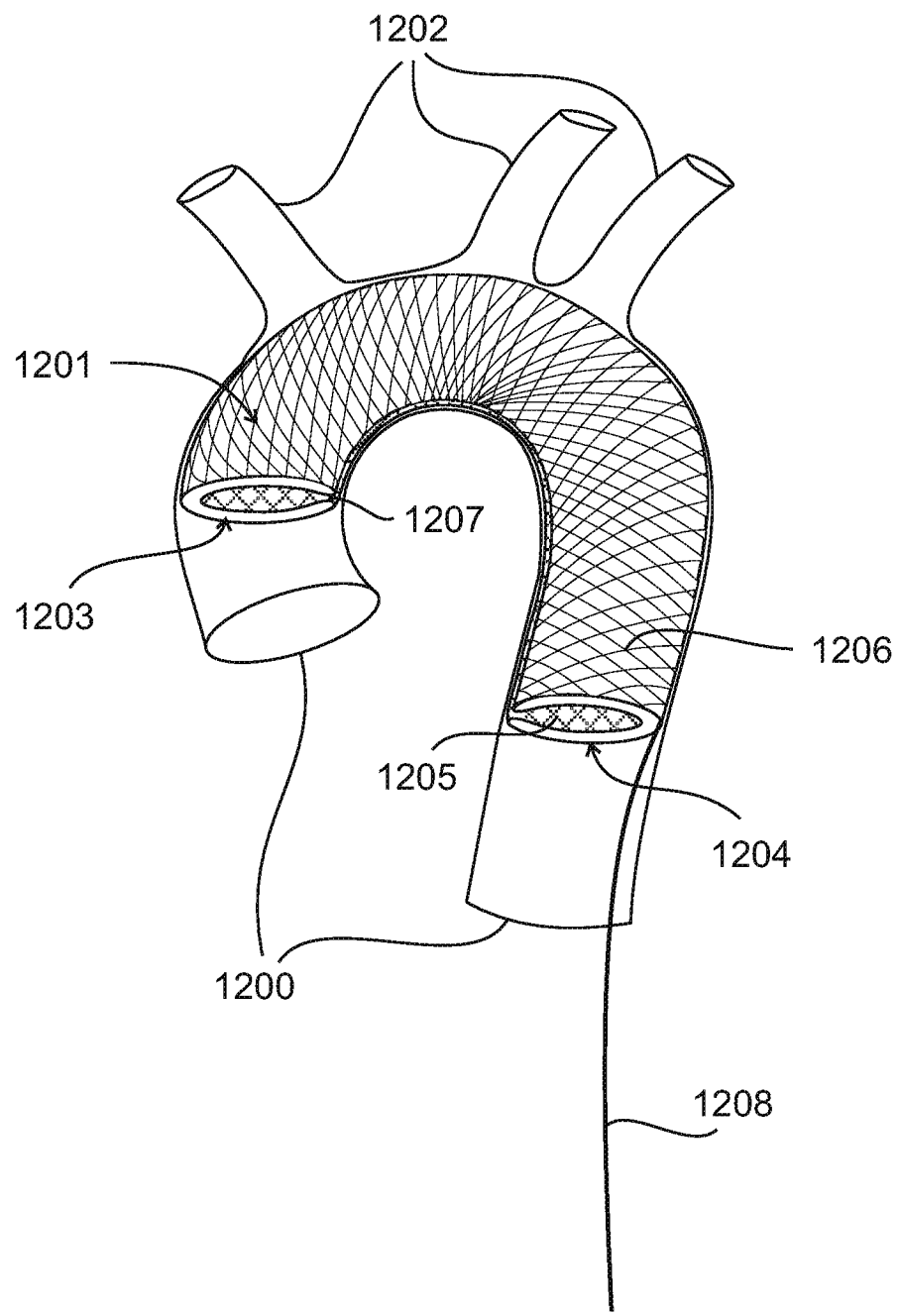
FIG. 12 is a simplified line drawing illustration of an aortic protection device according to an example embodiment of the invention, located in an aorta.

Example Embodiments of an Aortic Protection Device with a Horseshoe Shaped Cross Section Reference is now made to FIG. 12, which is a simplified line drawing illustration of an aortic protection device according to an example embodiment of the invention, located in an aorta.

FIG. 12 shows an aorta 1200, in which an aortic protection device 1201 is deployed. The aortic protection device 1201 includes at least one mesh layer 1206. FIG. 12 also shows aortic branches 1202.

In some embodiments the aortic protection device 1201 has a horseshoe-shaped cross section, as can be seen at a heart-proximal end 1203 of the aortic protection device 1201 and at a heart-distal end 1204 of the aortic protection device 1201. FIG. 12 shows a narrow open space 1207 which defined the horseshoe cross section of the aortic protection device 1201.

In some embodiments the aortic protection device 1201 includes a mesh coated with a porous polymer. In some embodiments the aortic protection device 1201 includes a metal mesh coated with polymer, and/or a metal mesh coated with polymer with mesh holes.

In some embodiments the aortic protection device 1201 includes two mesh layers 1206, 1205.

In some embodiments the aortic protection device 1201 includes a flexible outer mesh 1206 and an additional inner mesh 1205, as described above with reference to FIG. 8A.

In some embodiments the aortic protection device 1201 includes three layers of mesh, as described above with reference to FIG. 8B.

In some embodiments the aortic protection device 1201 is optionally attached to a control wire 1208 and optionally a catheter (not shown) during deployment.

In some embodiments, the horseshoe shaped cross section of the aortic protection device 1201 enables passing tools for operation on a heart side by side with a deployed aortic protection device 1201. In some embodiments, the horseshoe shaped cross section of the aortic protection device 1201 enables passing tools for operation on the heart, side by side with a deployed aortic protection device 1201, optionally of a diameter up to an entire diameter of an aorta.

Example Embodiments of a Coil-Supported Aortic Protection Device

Figures 13A, 13B:
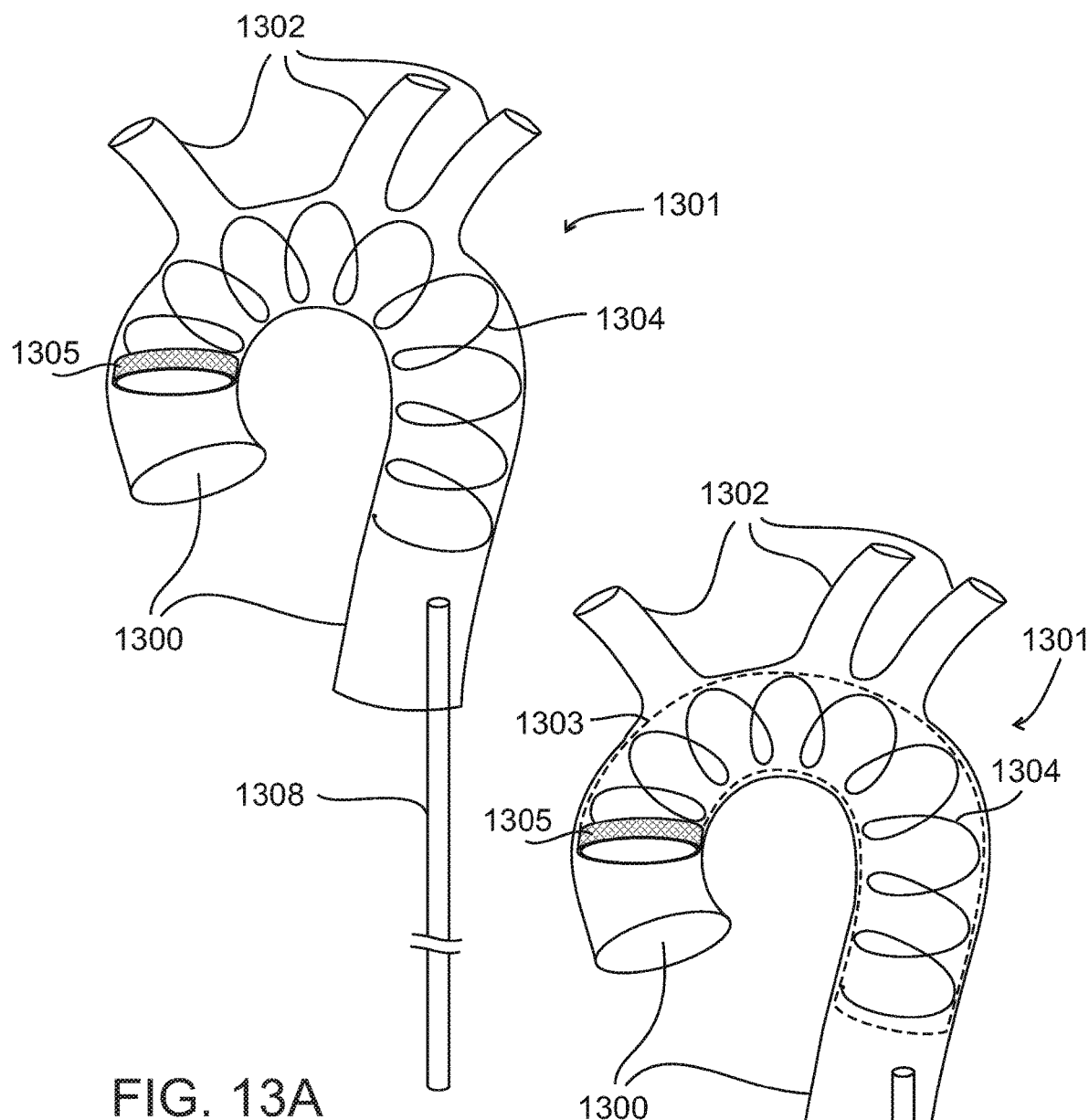
FIGS. 13A and 13B are simplified line drawing illustrations of an aortic protection device according to an example embodiment of the invention.

Reference is now made to FIGS. 13A and 13B, which are simplified line drawing illustrations of an aortic protection device according to an example embodiment of the invention.

FIGS. 13A and 13B show an aorta 1300 and aortic branches 1302.

FIG. 13A shows components of an aortic protection device 1301, including a shape memory material coil 1304 deployed in the aorta 1302 and a catheter 1306 through which the coil 1304 was optionally deployed.

In some embodiments the coil 1304 optionally includes a ring 1305, optionally at a heart-proximal end of the coil 1304. In some embodiments the ring 1305 is shaped and sized to expand against walls of the aorta 1300, optionally anchoring the coil 1304 in the aorta 1300.

FIG. 13B shows a mesh 1303, also a component of the aortic protection device 1301, deployed surrounding the coil 1304.

In some embodiments the mesh 1303 is optionally deployed through the catheter 1308.

Figure 13C:
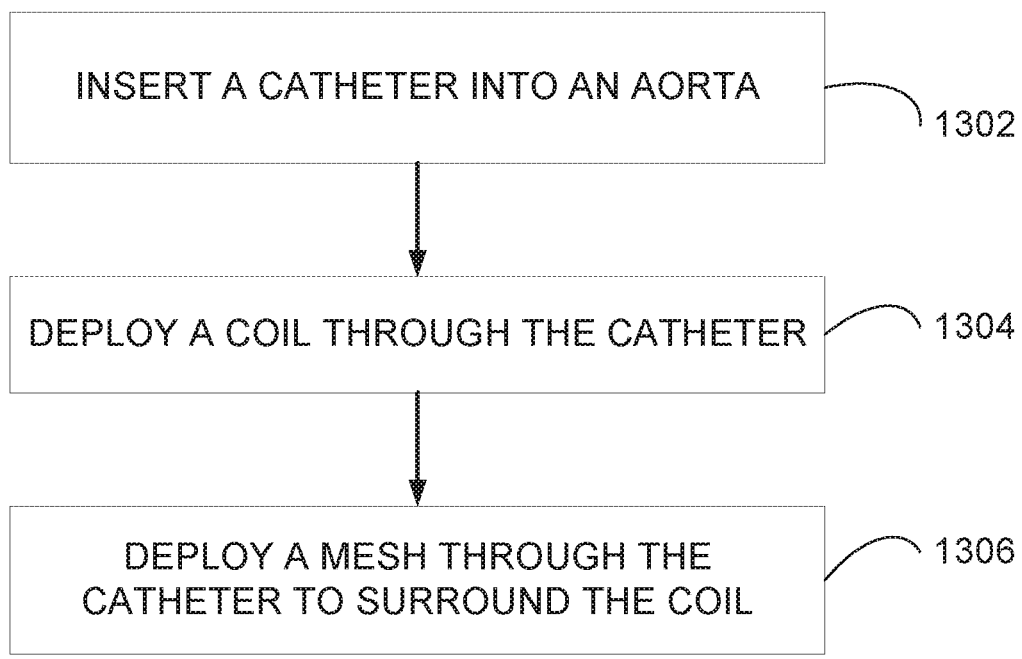
FIG. 13C is a simplified flow chart illustration of an example method of deploying the aortic protection device of FIGS. 13A and 13B.

Reference is now made to FIG. 13C, which is a simplified flow chart illustration of an example method of deploying the aortic protection device of FIGS. 13A and 13B.

FIG. 13C describes a method for deploying the aortic protection device of FIGS. 13A and 13B, including:

inserting a catheter into an aorta (1312);
deploying a coil through the catheter (1314); and
deploying a mesh through the catheter, to surround the coil (1316);

In some embodiments, the mesh is deployed before an operation on a heart, such as a heart valve operation or a TAVI operation.

In some embodiments the coil is deployed in a compressed form, optionally through a catheter having a diameter of 7 to 8 French. In some embodiments the coil is deployed in a compressed form, optionally through a catheter having a diameter in a range of 6-10 French.

In some embodiments the mesh is deployed through a same catheter as the coil.

In some embodiments the coil is optionally retrieved through a second catheter having a diameter of 12 to 16 French.

In some embodiments the mesh is deployed through a same second catheter used for retrieving the coil.

Example Embodiments of an Aortic Protection Device used to Perform Suction

Figure 14:
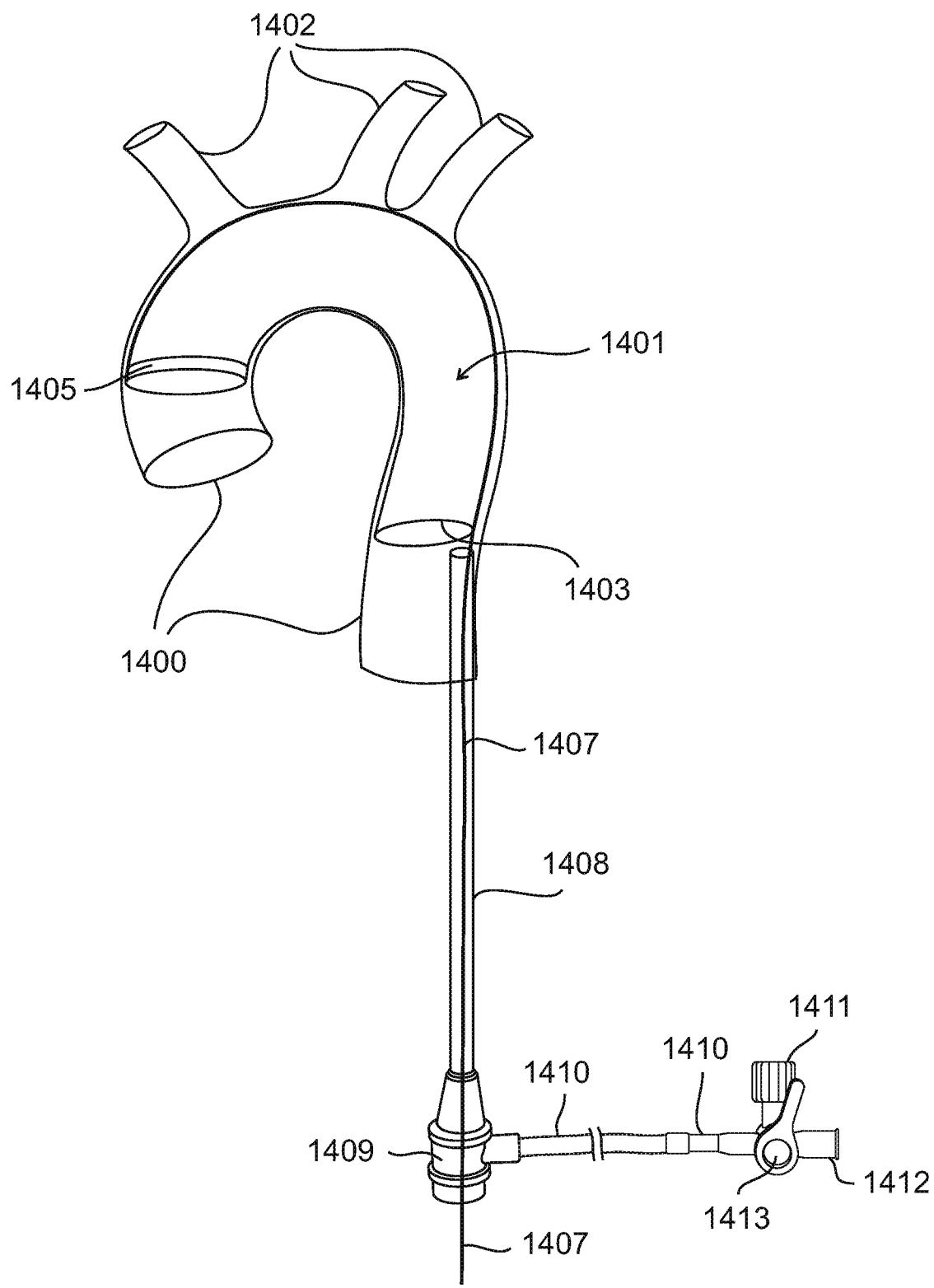
FIG. 14 is a simplified line drawing illustration of an aortic protection device and a catheter located in an aorta according to an example embodiment of the invention.

Reference is now made to FIG. 14, which is a simplified line drawing illustration of an aortic protection device and a catheter located in an aorta according to an example embodiment of the invention.

FIG. 14 shows an aorta 1400, in which an aortic protection device 1401 and a catheter 1408 are deployed. FIG. 14 also shows aortic branches 1402.

FIG. 14 also shows a side port 1409 at an outside-the-body end of the catheter 1408, which enables passing a control wire 1407 through the catheter 1408 and also enables performing suction through a side tube 1410. In some embodiments the side tube 1410 also includes a valve 1413 which controls passage from entrances 1411 1412 to the side tube 1310.

In some embodiments one of the entrances 1411 1412 is optionally connected to low pressure for providing suction of blood though the catheter 1408 when the valve 1413 is in a position which enables connection of suction to the side tube 1410.

In some embodiments providing suction to draw blood down the aorta 1400 is optionally performed while a heart operation is performed, or even extending after the heart operation is performed, in order to potentially draw blood with debris faster down the aorta, even draw the blood all the way out of the body.

In some embodiments 60-80 cubic centimeters of blood are drawn out of a patient's body during the suction.

In some embodiments the catheter 1408 is placed near to a downstream end 1403 of the aortic protection device 1401, as shown in FIG. 14, in order to perform suction.

In some embodiments the catheter 1408 is placed next to a downstream end 1403 of the aortic protection device 1401, at a distance in a range of 0-30 millimeters away from the downstream end 1403 of the aortic protection device 1401, in order to perform suction.

In some embodiments the catheter 1408 is placed just inside (not shown) the downstream end 1403 of the aortic protection device 1401, in order to perform suction.

In some embodiments the catheter 1408 is placed a distance in a range of 0-30 millimeters inside (not shown) the downstream end 1403 of the aortic protection device 1401, in order to perform suction.

In some embodiments the aortic protection device 1401 includes a heart-proximal ring 1405, optionally anchoring the aortic protection device 1401 to the aorta 1400 walls.

It is expected that during the life of a patent maturing from this application many relevant shape memory materials will be developed and the scope of the terms shape memory material and Nitinol are intended to include all such new technologies a priori.

It is expected that during the life of a patent maturing from this application many relevant flexible and/or stretchable materials will be developed and the scope of the term mesh material is intended to include all such new technologies a priori.

As used herein the term "about" refers to ±20%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range.

For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An aortic protection device comprising:
   a heart-proximal ring; and
   a mesh lumen portion connected to the heart proximal ring, shaped and sized to extend along the aorta, from a heart-side of a brachiocephalic artery exit from the aorta to distal of a left subclavian artery exit from the aorta, and
   a mechanism for changing a porosity of mesh pores in response to external control of a control wire attached to a heart-proximal end of the mesh lumen portion and a control wire attached to a more heart-distal part of the mesh lumen portion, while said mesh lumen remains anchored to the aorta in a manner which allows filtering of blood- borne debris from passing through said arteries;
   wherein the mesh lumen portion is arranged to change a porosity of the mesh pores to completely block blood from entering side arteries.

2. The device of claim 1, wherein the mesh lumen portion is arranged to change the porosity of the mesh pores in response to manipulating a proximal end of the mesh lumen portion relative to a distal end of the mesh lumen portion.

3. The device of claim 1, wherein the mesh lumen portion is arranged to change the porosity of the mesh pores in response to twisting a proximal end of the mesh lumen portion relative to a distal end of the mesh lumen portion.

4. The device of claim 1, wherein the mesh lumen portion is arranged to be reshaped as a narrower lumen in response to external control.

5. The device of claim 1, in which the mesh lumen portion is arranged to change a porosity from pores sized in a range between 200 microns to 100 microns to pores sized in a range between 100 to 10 microns.

6. The device of claim 1, in which the mesh lumen portion comprises a first mesh lumen comprising shape-memory material and a second mesh lumen comprising flexible material co-axial with the first mesh lumen.

7. The device of claim 6, in which the first mesh lumen is not attached to the second mesh lumen along most of a length of the first mesh lumen.

8. The device of claim 6, in which a flexible material outside mesh lumen has a greater diameter than a shape memory inside mesh lumen, enabling the outside mesh lumen to extend into arteries branching off the aorta.

9. The device of claim 6, in which a flexible material inside mesh lumen is shaped to contract away from a shape memory outside mesh lumen, reducing pore size of the flexible material inside mesh lumen.

10. The device of claim 6, in which the first mesh lumen is arranged to form an elongated shape with a horseshoe shaped cross section relative to a longitudinal direction of the lumen.

11. The device of claim 1, in which the mesh lumen portion comprises two flexible mesh lumens, one within another and co-axial.

12. The device of claim 1, in which the mesh lumen portion comprises:
   a first mesh lumen comprising shape-memory material;
   a second mesh lumen comprising flexible material; and
   a third mesh lumen comprising flexible material,
   wherein the second mesh lumen and the third mesh lumen are co-axial with the first mesh lumen.

13. The device of claim 1, in which the mesh lumen is produced by weaving polymer threads.

14. The device of claim 1 arranged to change porosity after the anchoring and the deploying.

15. The device of claim 1 comprising a wire arranged for removing the device from a patient body, the wire sized to extend from the aorta to external to a patient's body.

16. The aortic protection device of claim 1, wherein the heart-proximal ring is configured to remain expanded against the walls of the aorta even when the mesh lumen is made narrow.

17. A method of protecting a patient from blood-borne debris, comprising:
   anchoring an aortic protection device comprising anchoring a heart-proximal ring connected to a mesh lumen portion at a heart-side of a brachiocephalic artery exit from an aorta;
   deploying the mesh lumen to extend to distal of a left subclavian artery exit from the aorta, and
   controlling the mesh lumen to decrease porosity of the mesh pores during a heart operation, while the aortic protection device remains anchored and deployed such that the mesh lumen filters blood flow to arteries branching off the aorta and blocks at least some blood-borne debris from entering thereto, thereby protecting the patient from blood-borne debris;
   wherein the controlling comprises completely blocking blood from entering side arteries.

18. The method of claim 17, wherein the controlling comprises manipulating a proximal end of the mesh lumen portion relative to a distal end of the mesh lumen portion.

19. The method of claim 17, wherein the controlling comprises reshaping the mesh lumen portion as a narrower lumen than when anchoring the heart-proximal ring, retracting toward a center of the aorta.

20. The method of claim 17, in which the controlling the mesh lumen to change porosity of the mesh pores comprises changing porosity from pores sized in a range between 200 microns to 100 microns to pores sized to a range less than 100 microns.

21. The method of claim 17, wherein the controlling comprises decreasing pore size just before performing a medical procedure on a heart which may dislodge debris.

22. The method of claim 17, wherein the controlling comprises increasing pore size after performing a medical procedure on a heart which may dislodge debris.

23. The method of claim 17, comprising maintaining the decreased porosity over a time which overlaps with manipulation of a cardiac structure.

24. The method of claim 23, wherein said manipulation comprises an implantation or repair of a cardiac valve.

25. The method of claim 23, wherein said deploying comprises deploying after a medical procedure on the heart has started and comprising maintaining the decreased porosity during at least part of a surgical operation on a heart or heart valve.

* * * * *